United States Patent
Zhang et al.

(10) Patent No.: US 12,234,222 B2
(45) Date of Patent: Feb. 25, 2025

(54) PIPERAZINE AMIDE DERIVATIVE, PREPARATION METHOD THEREFOR, AND USE THEREOF IN MEDICINE

(71) Applicant: ZHEJIANG HISUN PHARMACEUTICAL CO., LTD., Zhejiang (CN)

(72) Inventors: Panpan Zhang, Zhejiang (CN); Sunli Yan, Zhejiang (CN); Ying Li, Zhejiang (CN); Chenli Guo, Zhejiang (CN); Wenjian Qian, Zhejiang (CN); Cheng Ye, Zhejiang (CN); Zhengzheng Shi, Zhejiang (CN); Taishan Hu, Zhejiang (CN); Lei Chen, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 753 days.

(21) Appl. No.: 17/602,758

(22) PCT Filed: Apr. 9, 2020

(86) PCT No.: PCT/CN2020/083854
§ 371 (c)(1),
(2) Date: Oct. 10, 2021

(87) PCT Pub. No.: WO2020/207419
PCT Pub. Date: Oct. 15, 2020

(65) Prior Publication Data
US 2022/0177450 A1 Jun. 9, 2022

(30) Foreign Application Priority Data
Apr. 12, 2019 (CN) .......................... 201910294193.9

(51) Int. Cl.
*C07D 401/14* (2006.01)
*C07D 403/14* (2006.01)
*C07D 487/08* (2006.01)
*C07D 498/08* (2006.01)

(52) U.S. Cl.
CPC ......... *C07D 401/14* (2013.01); *C07D 403/14* (2013.01); *C07D 487/08* (2013.01); *C07D 498/08* (2013.01)

(58) Field of Classification Search
CPC .. C07D 401/14; C07D 403/14; C07D 487/08; C07D 498/08
USPC .................................................. 514/230.5
See application file for complete search history.

(56) References Cited

U.S. PATENT DOCUMENTS

2017/0121312 A1  5/2017  Brubaker et al.

FOREIGN PATENT DOCUMENTS

| CN | 103242341 A    | 8/2013  |
|----|----------------|---------|
| CN | 108473468 A    | 8/2018  |
| JP | 2018-535967 A  | 12/2018 |
| TW | 201904974 A    | 2/2019  |
| WO | 2005/123697 A1 | 12/2005 |
| WO | 2016127074 A1  | 8/2016  |
| WO | 2017011776 A1  | 1/2017  |
| WO | 2017079140 A1  | 5/2017  |
| WO | 2017161269 A1  | 9/2017  |
| WO | 2018017983 A1  | 1/2018  |
| WO | 2018022761 A1  | 2/2018  |
| WO | 2018071454 A1  | 4/2018  |
| WO | 2018136661 A1  | 7/2018  |
| WO | 2018136663 A1  | 7/2018  |

OTHER PUBLICATIONS

First Office Action dated Oct. 18, 2022 for Japanese patent application No. 2021-559916, English translation provided by Global Dossier.
Tiansheng Wang et al., "Mtb PKNA/PKNB Dual Inhibition Provides Selectivity Advantages for Inhibitor Design To Minimize Host Kinase Interactions", ACS Medicinal Chemistry Letters, 2017, vol. 8, p. 1224-1229.
International Search Report for PCT/CN2020/083854 mailed Jul. 14, 2020, ISA/CN.

*Primary Examiner* — Kristin A Vajda
(74) *Attorney, Agent, or Firm* — Yue (Robert) Xu; Apex Attorneys at Law, LLP

(57) ABSTRACT

The present invention relates to a piperazine amide derivative as represented by formula (I) or a pharmaceutically acceptable salt thereof, and a pharmaceutical composition thereof, and use of same as a therapeutic agent, especially as a selective Rearranged During Transfection (RET) kinase inhibitor. Ring a, ring e, $X^1$, $X^2$, $X^3$, $X^4$, $R^1$, $R^2$, $R^3$, $R^4$, $R^{4'}$, $R^5$, $R^{5'}$, $R^6$, $R^{6'}$, $R^7$, $R^{7'}$, $R^8$, m and n have the same definitions as those in the specification.

(I)

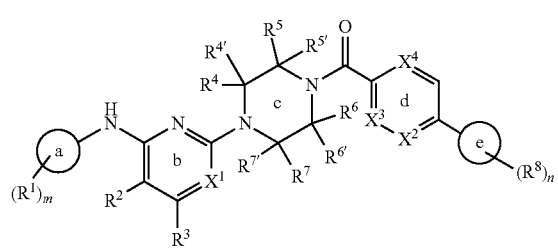

14 Claims, No Drawings

PIPERAZINE AMIDE DERIVATIVE, PREPARATION METHOD THEREFOR, AND USE THEREOF IN MEDICINE

This application is the national phase of International Application No. PCT/CN2020/083854 titled "PIPERAZINE AMIDE DERIVATIVE, PREPARATION METHOD THEREFOR, AND USE THEREOF IN MEDICINE", which claims the priority of Chinese Patent Application No. 201910294193.9, filed with the China National Intellectual Property Administration on Apr. 12, 2019, titled with "PIPERAZINE AMIDE DERIVATIVE, PREPARATION METHOD THEREFOR, AND USE THEREOF IN MEDICINE", which are hereby incorporated by reference in entirety.

FIELD

The present disclosure relates to the field of medicine technology, and specifically relates to a new piperazine amide derivative, a pharmaceutical composition comprising the derivative, and use thereof as a therapeutic agent, especially as a selective Rearranged during transfection (RET) kinase inhibitor.

BACKGROUND

Rearranged during transfection gene (RET gene) is a proto-oncogene that encodes a tyrosine kinase receptor in the human body and regulates cell reproduction and survival. This gene is activated by the interaction with glial cell-derived neurotrophic factor family receptors and a receptors of the family to form a dimer. Through phosphorylation, it regulates signal pathways, exercises the functions of signaling and regulating life activities. Abnormal expression of RET gene is associated with a variety of cancer diseases. The gene fused with other genes through chromosomal rearrangement or experiencing site-directed mutation can be continuously in activated state independently of ligands, leading to abnormal signaling pathways, thereby causing excessive cell proliferation and cancer.

In recent years, more and more evidences have shown that the fusion and mutation of RET gene are the driving force of some cancers, and RET gene does not coincide with other driver genes, presenting significant specificity. RET gene fusion is common in papillary thyroid cancer and non-small cell lung cancer. For example, 30% of sporadic papillary thyroid cancer, 70% of radiation-induced papillary thyroid cancer, and about 2% of non-small cell lung cancer are driven by RET gene fusion. RET gene mutation is common in medullary thyroid cancer. For example, more than 50% of medullary thyroid cancer and almost all congenital medullary cancer and multiple endocrine adenomatosis are caused by site-directed mutations in RET gene.

Current treatment methods mainly use multi-target kinase inhibitors with RET kinase inhibitory activity to treat cancer patients with RET gene fusion or mutation. However, under these conditions, due to off-target effects and drug toxicity, the dose of the drug is insufficient to achieve a level sufficient to inhibit abnormal expression of RET gene. In addition, in the process of cancer treatment, cancer cells will develop drug resistance through mutations. Once drug resistance occurs, the patient's treatment options will become very limited. Therefore, there is a great need for a selective RET kinase inhibitor to treat patients with RET gene fusion or mutation.

There are no drugs that selectively target RET kinase on the market. A series of patents about selective RET kinase inhibitors have been published, including WO2016127074, WO2017079140, WO2017011776, WO2017161269, WO2018017983, WO2018022761, WO2018071454, WO2018136661, WO2018136663, etc. The drugs currently in clinical trials are Blu-667, Loxo-292 and GSK-3352589. However, these are far from enough for anti-tumor research. It is still necessary to research and develop new selective RET kinase inhibitors to address the unmet medical needs.

SUMMARY

In order to overcome the shortcomings of the prior art, in the first aspect, the present disclosure provides a compound represented by formula (I), or a stereoisomer or tautomer thereof, or a pharmaceutically acceptable salt thereof:

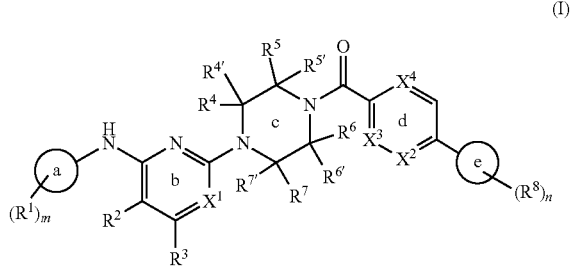

(I)

wherein
ring a is selected from pyrazolyl, pyridyl and pyridonyl;
$R^1$ is selected from hydrogen, $C_1$-$C_3$ alkyl, and $C_3$-$C_6$ cycloalkyl, wherein the $C_1$-$C_3$ alkyl and $C_3$-$C_6$ cycloalkyl are optionally further substituted with one or more halogen atoms;
$X^1$ is selected from CH and N;
$R^2$ is selected from hydrogen and $C_1$-$C_6$ alkyl;
$R^3$ is selected from hydrogen, cyano, $C_1$-$C_6$ alkyl, $C_1$-$C_5$ primary alcohol group, $C_3$-$C_7$ tertiary alcohol group, $C_1$-$C_3$ alkoxy, $C_3$-$C_6$ cycloalkyl, and —$R^9CO_2R^{10}$, wherein the $C_1$-$C_6$ alkyl, $C_1$-$C_5$ primary alcohol group, $C_3$-$C_7$ tertiary alcohol group, $C_1$-$C_3$ alkoxy, and $C_3$-$C_6$ cycloalkyl are optionally further substituted with one or more halogen atoms;
alternatively, $R^2$, $R^3$ and the two carbon atoms attached thereto together form an aryl group, which is optionally further substituted with one or more halogen atoms or $C_1$-$C_6$ alkyl;
$R^9$ is selected from a chemical bond and $C_1$-$C_4$ alkylene group;
$R^{10}$ is selected from hydrogen and $C_1$-$C_6$ alkyl;
$X^2$, $X^3$, and $X^4$ are selected from CH and N; when $X^2$ is N, at most one of $X^3$ and $X^4$ is N; when $X^2$ is CH, $X^3$ and $X^4$ are both CH;
$R^4$, $R^{4'}$, $R^5$, $R^{5'}$, $R^6$, $R^{6'}$, $R^7$, and $R^{7'}$ are independently selected from hydrogen, $C_1$-$C_3$ alkyl and $C_1$-$C_4$ alkoxy, wherein the $C_1$-$C_3$ alkyl is optionally further substituted with one or more hydroxy, carboxy or cyano groups;
alternatively, $R^4$ and $R^{4'}$, $R^5$ and $R^{5'}$, $R^6$ and $R^{6'}$, or $R^7$ and $R^{7'}$ are attached together to form —(CH$_2$)$_2$—, —(CH$_2$)$_3$—, —CH(CH$_3$)CH$_2$—, —OCH$_2$CH$_2$—, or —CH$_2$OCH$_2$—;
alternatively, $R^4$ and $R^5$, $R^4$ and $R^6$, $R^4$ and $R^7$, $R^{4'}$ and $R^{5'}$, $R^{4'}$ and $R^6$, $R^{4'}$ and $R^{7'}$, $R^5$ and $R^6$, $R^5$ and $R^7$, $R^{5'}$ and $R^{6'}$, $R^{5'}$ and $R^{7'}$, $R^6$ and $R^7$, or $R^{6'}$ and $R^{7'}$ are attached together to form —(CH$_2$)q- or —(CH$_2$OCH$_2$)—;

alternatively, $R^4$ and $R^{4'}$, $R^5$ and $R^{5'}$, $R^6$ and $R^{6'}$, or $R^7$ and $R^{7'}$ together represent =O;

ring e is selected from pyrazolyl, pyridyl, phenyl and 3-azabicyclo[3.1.0]hexane-3-yl;

$R^8$ is independently selected from hydrogen, halogen, cyano, $C_1$-$C_3$ alkyl, $C_1$-$C_3$ alkoxy, and $C_3$-$C_6$ cycloalkyl, wherein the $C_1$-$C_3$ alkyl, $C_1$-$C_3$ alkoxy, and $C_3$-$C_6$ cycloalkyl are optionally further substituted with one or more halogen atoms;

m is 1 or 2;

n is 1, 2 or 3; and q is 2 or 3.

In a preferred embodiment of the present disclosure, there is provided a compound represented by formula (I), or a stereoisomer or tautomer thereof, or a pharmaceutically acceptable salt thereof, which is a compound represented by formula (II), or a stereoisomer or tautomer thereof, or a pharmaceutically acceptable salt thereof:

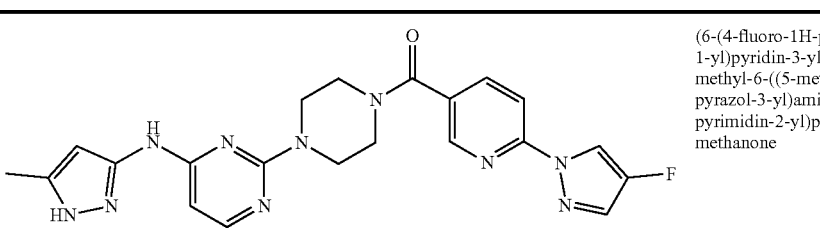

(II)

wherein ring e, $X^1$, $X^2$, $X^3$, $X^4$, $R^1$, $R^2$, $R^3$, $R^4$, $R^{4'}$, $R^5$, $R^{5'}$, $R^6$, $R^{6'}$, $R^7$, $R^{7'}$, $R^8$, m, and n have the same definitions as in formula (I).

In a preferred embodiment of the present disclosure, there is provided a compound represented by formula (I) or formula (II), or a stereoisomer or tautomer thereof, or a pharmaceutically acceptable salt thereof, wherein $R^3$ is selected from hydrogen, cyano, $C_1$-$C_6$ alkyl, hydroxymethyl, hydroxyisopropyl, $C_1$-$C_3$ alkoxy, $C_3$-$C_6$ cycloalkyl, and —$R^9CO_2R^{10}$, wherein the $C_1$-$C_6$ alkyl, hydroxymethyl, hydroxyisopropyl, $C_1$-$C_3$ alkoxy, and $C_3$-$C_6$ cycloalkyl are optionally further substituted with one or more halogen atoms; alternatively, $R^2$, $R^3$ and the two carbon atoms attached thereto together form an aryl group, which is optionally further substituted with one or more halogen atoms or $C_1$-$C_6$ alkyl; $R^9$ is selected from a chemical bond or $C_1$-$C_4$ alkylene group; $R^{10}$ is selected from hydrogen and $C_1$-$C_6$ alkyl.

In a preferred embodiment of the present disclosure, there is provided a compound represented by formula (I) or formula (II), or a stereoisomer or tautomer thereof, or a pharmaceutically acceptable salt thereof, wherein $R^3$ is selected from hydrogen, methyl, trifluoromethyl, hydroxymethyl, hydroxyisopropyl, —COOH and —COOMe; alternatively, $R^2$, $R^3$ and the two carbon atoms attached thereto together form a benzene ring.

In a preferred embodiment of the present disclosure, there is provided a compound represented by formula (I) or formula (II), or a stereoisomer or tautomer thereof, or a pharmaceutically acceptable salt thereof, wherein $R^4$, $R^{4'}$, $R^5$, $R^{5'}$, $R^6$, $R^{6'}$, $R^7$, and $R^{7'}$ are each independently selected from hydrogen, methyl, —$CH_2OH$ and —$CH_2CH_2OH$; alternatively, $R^4$ and $R^{4'}$, $R^5$ and $R^{5'}$, $R^6$ and $R^{6'}$, or $R^7$ and $R^{7'}$ are attached together to form —$(CH_2)_2$—, —$OCH_2CH_2$— or —$CH_2OCH_2$—; alternatively, $R^4$ and $R^5$, $R^4$ and $R^6$, $R^4$ and $R^7$, $R^{4'}$ and $R^{5'}$, $R^{4'}$ and $R^{6'}$, $R^{4'}$ and $R^{7'}$, $R^5$ and $R^6$, $R^5$ and $R^7$, $R^{5'}$ and $R^{6'}$, $R^{5'}$ and $R^{7'}$, $R^6$ and $R^7$, or $R^{6'}$ and $R^{7'}$ are attached together to form —$CH_2OCH_2$— or —$(CH_2)_2$—.

In a preferred embodiment of the present disclosure, there is provided a compound represented by formula (I) or formula (II), or a stereoisomer or tautomer thereof, or a pharmaceutically acceptable salt thereof, wherein $R^8$ is independently selected from hydrogen, halogen, cyano and $C_1$-$C_3$ alkyl, wherein the halogen is fluorine or chlorine, and the $C_1$-$C_3$ alkyl is methyl.

The specific structure of the compound represented by formula (I) of the present disclosure includes, but is not limited to:

| Compound No. | Structural formula | Nomenclature |
|---|---|---|
| I-1 | 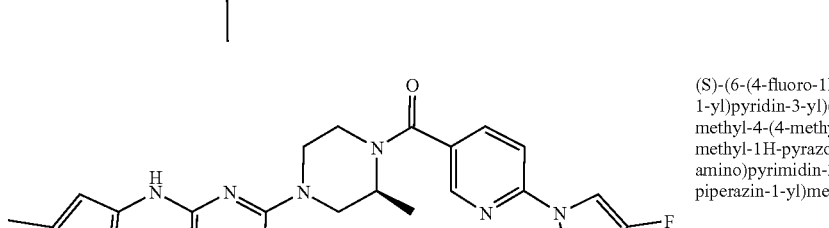 | (6-(4-fluoro-1H-pyrazol-1-yl)pyridin-3-yl)(4-(4-methyl-6-((5-methyl-1H-pyrazol-3-yl)amino)pyrimidin-2-yl)piperazin-1-yl)methanone |
| I-2 |  | (S)-(6-(4-fluoro-1H-pyrazol-1-yl)pyridin-3-yl)(2-methyl-4-(4-methyl-6-((5-methyl-1H-pyrazol-3-yl)amino)pyrimidin-2-yl)piperazin-1-yl)methanone |

| Compound No. | Structural formula | Nomenclature |
|---|---|---|
| I-3 | 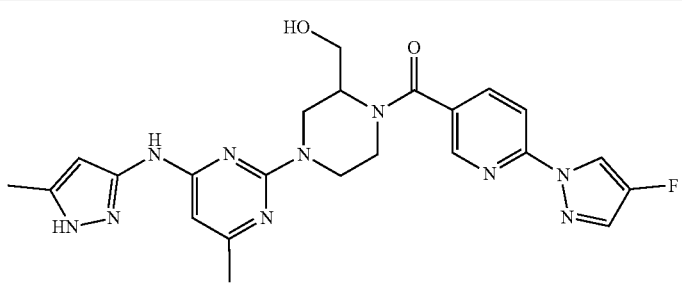 [SMILES: Cc1cc(Nc2cc(C)[nH]n2)nc(N2CCN(C(=O)c3ccc(-n4cc(F)cn4)nc3)C(CO)C2)n1] | (6-(4-fluoro-1H-pyrazol-1-yl)pyridin-3-yl)(2-(hydroxymethyl)-4-(4-methyl-6-(5-methyl-1H-pyrazol-3-yl)amino)pyrimidin-2-yl)piperazin-1-yl)methanone |
| I-4 | 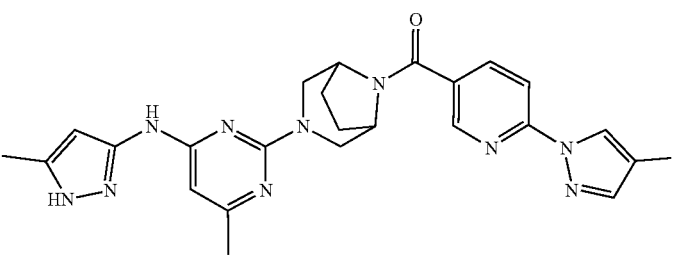 | (6-(4-fluoro-1H-pyrazol-1-yl)pyridin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-5 | 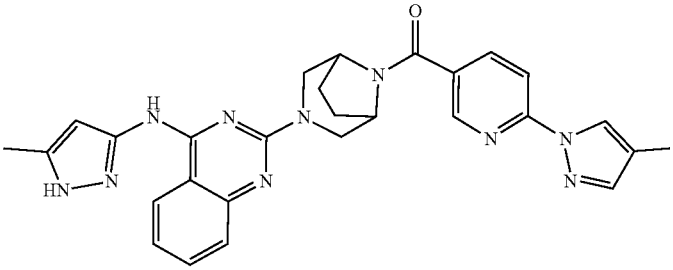 | (6-(4-fluoro-1H-pyrazol-1-yl)pyridin-3-yl)(3-(4-((5-methyl-1H-pyrazol-3-yl)amino)quinazoline-2-yl)-3,8-diazabicyclo[3.2.1]octane-8-yl)methanone |
| I-6 | 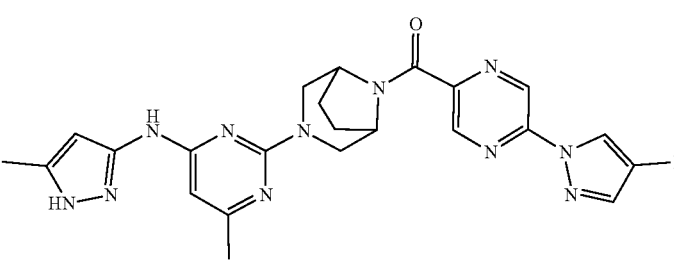 | (5-(4-fluoro-1H-pyrazol-1-yl)pyrazine-2-yl)(3-(4-methyl-6-((5-methyl-1H-pyrazol-3-yl)amino)pyrimidin-2-yl)-3,8-diazabicyclo[3.2.1]octane-8-yl)methanone |
| I-7 | 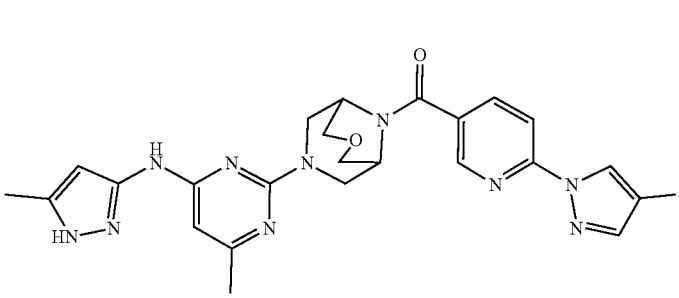 | (6-(4-fluoro-1H-pyrazol-1-yl)pyridin-3-yl)(7-(4-methyl-6-((5-methyl-1H-pyrazol-3-yl)amino)pyrimidin-2-yl)-3-oxa-7,9-diazabicyclo[3.3.1]nonane-9-yl)methanone |

-continued

| Compound No. | Structural formula | Nomenclature |
|---|---|---|
| I-8 | 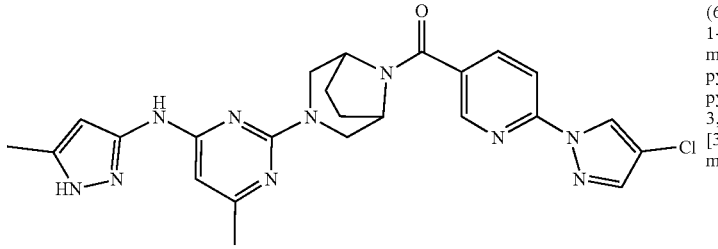 | (6-(4-chloro-1H-pyrazol-1-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-9 | 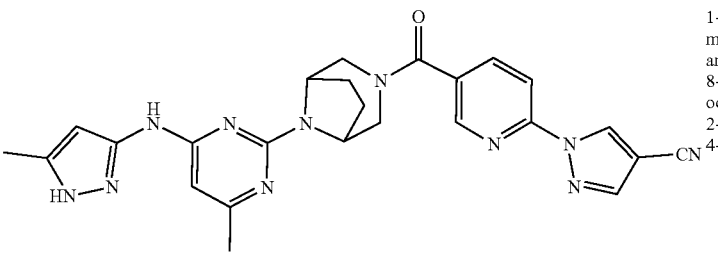 | 1-(5-(8-(4-methyl-6-(5-methyl-1H-pyrazol-3-yl)amino)pyrimidin-2-yl)-3,8-diazabicyclo[3.2.1]octane-3-carbonyl)pyridin-2-yl)-1H-pyrazol-4-carbonitrile |
| I-10 | 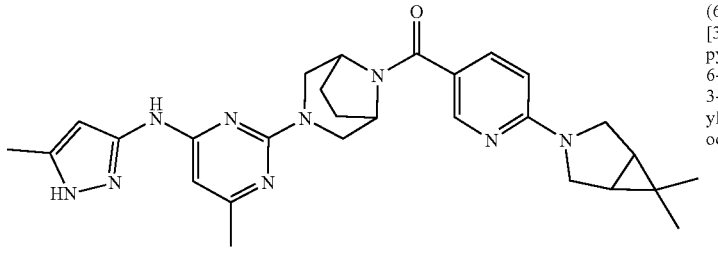 | (6-(6,6-dimethyl-3-azabicyclo[3.1.0]hexane-3-yl)pyridin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-11 | 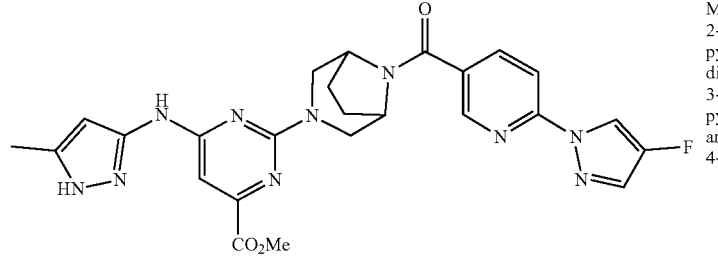 | Methyl 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-carboxylate |
| I-12 | 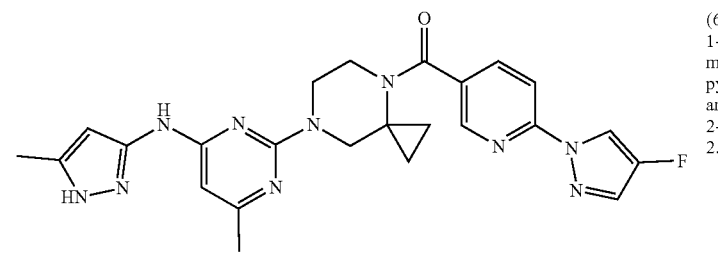 | (6-(4-fluoro-1H-pyrazol-1-yl)pyridin-3-yl)(7-(4-methyl-6-((5-methyl-1H-pyrazol-3-yl)amino)pyrimidin-2-yl)-4,7-diazaspiro[2.5]octane-4-yl)methanone |
| I-13 | 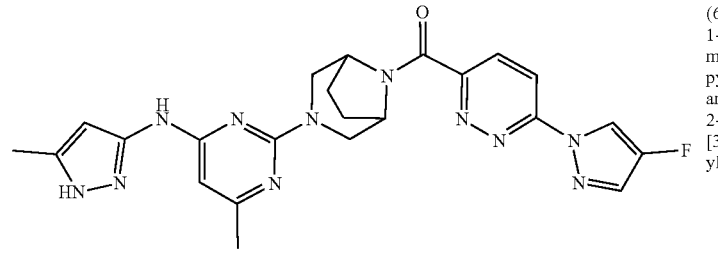 | (6-(4-fluoro-1H-pyrazol-1-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone |

-continued

| Compound No. | Structural formula | Nomenclature |
|---|---|---|
| I-14 | | (6-(4-fluoro-1H-pyrazol-1-yl)pyridin-3-yl)(3-(4-((5-methyl-1H-pyrazol-3-yl)amino)pyrimidin-2-yl)-3,8-diazabicyclo[3.2.1]octane-8-yl)methanone |
| I-15 | | (6-(4-fluoro-1H-pyrazol-1-yl)pyridazin-3-yl)(4-(4-methyl-6-((5-methyl-1H-pyrazol-3-yl)amino)pyrimidin-2-yl)piperazin-1-yl)methanone |
| I-16 | | (6-(4-fluoro-1H-pyrazol-1-yl)pyridazin-3-yl)(3-(4-((5-methyl-1H-pyrazol-3-yl)amino)-6-(trifluoromethyl)pyrimidin-2-yl)-3,8-diazabicyclo[3.2.1]octane-8-yl)methanone |
| I-17 | | (6-(4-chloro-1H-pyrazol-1-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-18 | | (6-(4-fluoro-1H-pyrazol-1-yl)pyridazin-3-yl)(9-(4-methyl-6-((5-methyl-1H-pyrazol-3-yl)amino)pyrimidin-2-yl)-3-oxa-7,9-diazabicyclo[3.3.1]nonane-7-yl)methanone |
| I-19 | | 2-(8-(6-(4-fluoro-1H-pyrazol-1-yl)nicotinoyl)-3,8-diazabicyclo[3.2.1]octane-3-yl)-6-(5-methyl-1H-pyrazol-3-yl)amino)pyrimidin-4-formic acid |

-continued

| Compound No. | Structural formula | Nomenclature |
|---|---|---|
| I-20 | 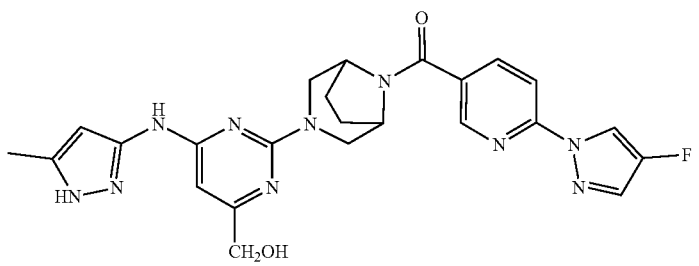 [SMILES: COC(=O)c1cc(Nc2cc(C)[nH]n2)nc(N2CC3CCC(C2)N3C(=O)c2ccc(-n3cc(F)cn3)nc2)n1] | (6-(4-fluoro-1H-pyrazol-1-yl)pyridin-3-yl)(3-(4-(hydroxymethyl)-6-((5-methyl-1H-pyrazol-3-yl)amino)pyrimidin-2-yl)-3,8-diazabicyclo[3.2.1]octane-8-yl)methanone |
| I-21 | 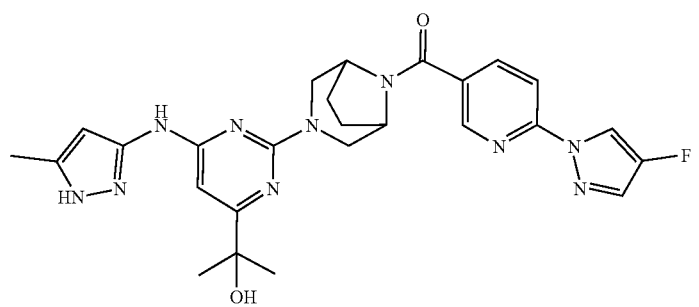 [SMILES: Cc1cc(Nc2cc(C(C)(C)O)nc(N3CC4CCC(C3)N4C(=O)c3ccc(-n4cc(F)cn4)nc3)n2)n[nH]1] | (6-(4-fluoro-1H-pyrazol-1-yl)pyridin-3-yl)(3-(4-(2-hydroxypropyl-2-yl)-6-((5-methyl-1H-pyrazol-3-yl)amino)pyrimidin-2-yl)-3,8-diazabicyclo[3.2.1]octane-8-yl)methanone |
| I-22 | 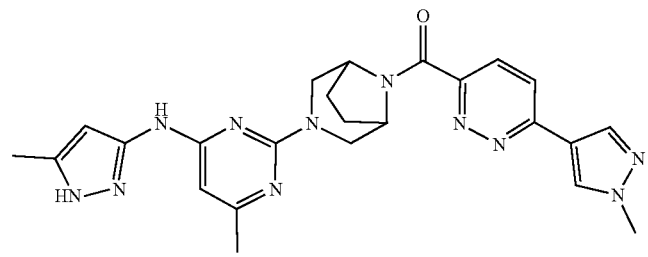 [SMILES: Cc1cc(Nc2cc(C)[nH]n2)nc(N2CC3CCC(C2)N3C(=O)c2ccc(-c3cnn(C)c3)nn2)n1] | (6-(1-methyl-1H-pyrazol 4-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-23 | 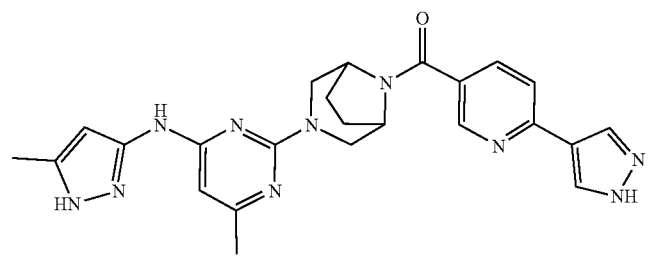 [SMILES: Cc1cc(Nc2cc(C)[nH]n2)nc(N2CC3CCC(C2)N3C(=O)c2ccc(-c3cn[nH]c3)nc2)n1] | (6-(1H-pyrazol-4-yl)pyridin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-24 | 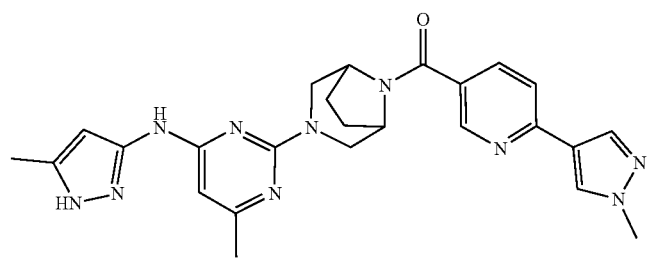 [SMILES: Cc1cc(Nc2cc(C)[nH]n2)nc(N2CC3CCC(C2)N3C(=O)c2ccc(-c3cnn(C)c3)nc2)n1] | (6-(1-methyl-1H-pyrazol-4-yl)pyridin-3-yl)(3-(4-methyl-6-((5-methyl-1H-pyrazol-3-yl)amino)pyrimidin-2-yl)-3,8-diazabiciyclo[3.2.1]octane-8-yl)methanone |

-continued

| Compound No. | Structural formula | Nomenclature |
|---|---|---|
| I-25 | | (6-(4-fluorophenyl)pyridin-3-yl)(3-(4-methyl-6-((5-methyl-1H-pyrazol-3-yl)amino)pyrimidin-2-yl)-3,8-diazabicyclo[3.2.1]octane 8-yl)methanone |
| I-26 | | (6-(4-fluorophenyl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone |
| I-27 | | (6-(4-fluorophenyl)pyridazin-3-yl)(4-(4-methyl-6-((5-methyl-1H-pyrazol-3-yl)amino)pyrimidin-2-yl)piperazin-1-yl)methanon |
| I-28 | | [2,4'-bipyridin]-5-yl(3-(4-methyl-6-((5-methyl-1H-pyrazol-3-yl)amino)pyrimidin-2-yl)-3,8-diazabicyclo[3.2.1]octane-8-yl)methanone |
| I-29 | | (3-(4-methyl-6-((5-methyl-1H-pyrazol-3-yl)amino)pyrimidin-2-yl)-3,8-diazabicyclo[3.2.1]octane-8-yl)(4-(pyridin-3-yl)phenyl)methanone |
| I-30 | | (6-(4-fluoro-1H-pyrazol-1-yl)pyridazin-3-yl)(8-(4-methyl-6-((5-methyl-1H-pyrazol-3-yl)amino)pyridin-2-yl)-3,8-diazabicyclo[3.2.1]octane-3-yl)methanone | or a stereoisomer or tautomer thereof, or a pharmaceutically acceptable salt thereof.

In another aspect, the present disclosure provides a pharmaceutical composition, comprising an effective dose of the compound represented by formula (I) or formula (II), or a stereoisomer or tautomer thereof, or a pharmaceutically acceptable salt thereof, and a pharmaceutically acceptable carrier, an excipient, or a combination thereof.

In yet another aspect, the present disclosure provides use of the compound represented by formula (I) or formula (II), or a stereoisomer or tautomer thereof, or a pharmaceutically acceptable salt thereof in the manufacture of a Rearranged during transfection kinase inhibitor.

In yet another aspect, the present disclosure provides a method for inhibiting Rearranged during transfection kinase, comprising administering the compound or pharmaceutical composition of the present disclosure to a subject in need thereof.

In yet another aspect, the present disclosure also provides a method for treating or preventing a disease related to or driven by Rearranged during transfection gene, comprising administering the compound or pharmaceutical composition of the present disclosure to a subject in need thereof.

In the above use or method of the present disclosure, the disease related to or driven by Rearranged during transfection gene is preferably a cancer, wherein the cancer is preferably lung cancer, thyroid cancer, colon cancer, breast cancer or pancreatic cancer.

Definitions

Some terms used in the specification and claims of the present disclosure are defined as follows:

When used as a group or part of a group, "alkyl" refers to a linear or branched aliphatic hydrocarbon group. Examples of alkyl group include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl can be substituted or unsubstituted. In the present disclosure, preferred alkyl is $C_1$-$C_6$ alkyl, and more preferred alkyl is $C_1$-$C_4$ alkyl or $C_1$-$C_3$ alkyl.

"Cycloalkyl" refers to saturated or partially saturated monocyclic, fused, bridged, and spirocyclic carbocyclic ring. Examples of monocyclic cycloalkyl group include, but are not limited to, cyclopropyl, cyclobutyl, cyclopentyl, cyclopentenyl, cyclohexyl, cyclohexenyl, cyclohexadienyl, etc., preferably cyclopropyl, cyclohexenyl. In the present disclosure, the preferred cycloalkyl is $C_3$-$C_6$ cycloalkyl.

"Aryl" refers to a carbocyclic aromatic system containing one or two rings, where the rings can be attached together in a fused manner. The term "aryl" includes aromatic groups such as phenyl, naphthyl, and tetrahydronaphthyl. Preferably, the aryl group is $C_6$-$C_{10}$ aryl; more preferably, the aryl group is phenyl and naphthyl, and most preferably phenyl.

"Alkoxy" refers to the "alkyl-O—" group. $C_1$-$C_6$ alkoxy, $C_1$-$C_4$ alkoxy or $C_1$-$C_3$ alkoxy are preferred. Examples include, but are not limited to: methoxy, ethoxy, n-propoxy, isopropoxy, n-butoxy, isobutoxy, tert-butoxy, etc.

"$C_1$-$C_5$ primary alcohol group" refers to a monovalent primary alcohol group containing 1-5 carbon atoms, examples of which include —$CH_2OH$, —$CH_2CH_2OH$, —$CH_2CH_2CH_2OH$, —$CH(CH_3)CH_2OH$, —$(CH_2)_4OH$, —$CH(CH_3)CH_2CH_2OH$, —$CH_2CH(CH_3)CH_2OH$, —$C(CH_3)_2CH_2OH$, —$(CH_2)_5OH$, —$CH_2CH_2CH(CH_3)CH_2OH$, —$CH_2CH(CH_3)CH_2CH_2OH$, —$CH(CH_3)CH_2CH_2CH_2OH$, —$CH_2C(CH_3)_2OH$, —$CH(CH_2OH)CH(CH_3)_2$, —$CH(CH_3)CH(CH_3)CH_2OH$.

"$C_3$-$C_7$ tertiary alcohol group" refers to a monovalent tertiary alcohol group containing 3-7 carbon atoms, examples of which include —$C(CH_3)_2OH$, —$CH_2C(CH_3)_2OH$, —$CH_2CH_2C(CH_3)_2OH$, —$CH(CH_3)C(CH_3)_2OH$, —$CH_2CH_2CH_2C(CH_3)_2OH$, —$CH_2CH(CH_3)C(CH_3)_2OH$, —$CH(CH_3)CH_2C(CH_3)_2OH$, —$C(CH_3)_2C(CH_3)_2OH$, —$(CH_2)_4C(CH_3)_2OH$, —$CH_2CH_2CH(CH_3)C(CH_3)_2OH$, —$CH_2CH(CH_3)CH_2C(CH_3)_2OH$, —$CH(CH_3)CH_2CH_2C(CH_3)_2OH$, —$CH(CH_3)CH(CH_3)C(CH_3)_2OH$, —$CH_2C(CH_3)_2C(CH_3)_2OH$, —$C(CH_3)_2CH_2C(CH_3)_2OH$.

"Hydroxy" refers to —OH. "Halogen" refers to fluorine, chlorine, bromine and iodine, preferably chlorine, bromine and fluorine. "Amino" refers to —$NH_2$. "Cyano" refers to —CN. "Benzyl" refers to —$CH_2$-phenyl. "Carboxy" refers to —C(O)OH. "Ester group" refers to —C(O)O(alkyl) or (cycloalkyl), wherein the definitions of alkyl and cycloalkyl are as described above. "DMSO" refers to dimethyl sulfoxide. "Boc" refers to tert-butoxycarbonyl. "DIPEA" refers to diisopropylethylamine. "$Pd_2(dba)_3$" refers to tris(dibenzylideneacetone)dipalladium. "t-BuXPhos" refers to 2-di-tert-butylphosphino-2',4',6'-triisopropylbiphenyl. "DMAc" refers to N,N-dimethylacetamide. "DMF" refers to N,N-dimethylformamide. "$PCy_3$" refers to tricyclohexylphosphine. "HATU" refers to 2-(7-azabenzotriazol-1-yl)-N,N,N',N'-tetramethyluronium hexafluorophosphate. "PyBOP" refers to benzotriazol-1-yl-oxytripyrrolidinyl phosphonium hexafluorophosphate. "$T_3P$" refers to propyl phosphoric anhydride. "Bpin" refers to boronic acid pinacol ester. "NMP" refers to N-methylpyrrolidone.

"Substituted" refers to one or more hydrogen atoms in a group, preferably up to 5, more preferably 1-3 hydrogen atoms, such as, 1 hydrogen atom, 2 hydrogen atoms or 3 hydrogen atoms, are independently substituted by a corresponding number of substituents. It goes without saying that the substituents are only in their possible chemical positions, and those skilled in the art can determine (by experiment or theory) possible or impossible substitutions without too much effort. For example, an amino group or a hydroxyl group having free hydrogen may be unstable when combined with a carbon atom having an unsaturated (e.g., olefinic) bond.

The definitions and conventions of stereochemistry in the present disclosure generally refer to the following documents: S. P. Parker, Ed., McGraw-Hill Dictionary of Chemical Terms (1984) McGraw-HillBook Company, New York; and Eliel, E. and Wilen, S., "Stereochemistry of Organic Compounds", John Wiley & Sons, Inc., New York, 1994. The compound of the present disclosure may contain asymmetric centers or chiral centers, so there are different stereoisomers. All stereoisomeric forms of the compound of the present disclosure, including but not limited to diastereomers, enantiomers, atropisomers and mixtures thereof, such as racemic mixtures, constitute part of the present disclosure. Diastereomers can be separated into individual diastereomers by methods such as chromatography, crystallization, distillation or sublimation based on their physical and chemical differences. Enantiomers can be obtained by separation: by converting a chiral isomeric mixture into a diastereomeric mixture through reaction with a suitable optically active compound (for example, a chiral auxiliary, such as a chiral alcohol or Mosher's acid chloride), separating diastereomers and converting the individual diastereomers to the corresponding pure enantiomers. The intermediates and compounds of the present disclosure may also exist in different tautomeric forms, and all such forms are included in the scope of the present disclosure. Many organic compounds exist in optically active forms, that is, they have the ability to deflect the plane of plane-polarized light. When describing optically active compounds, the prefixes D, L or R, S are used to indicate the absolute configuration of the chiral center of the molecule. The prefixes d, l or (+), (−) are used to name the symbols for the plane-polarized light deflection of the compound. (−) or l means that the compound is levorotatory, and the prefix (+) or d means that the compound is dextrorotatory. The atoms or atomic groups of these stereoisomers are attached to each other in the same order, but their stereostructures are different.

A specific stereoisomer may be an enantiomer, and a mixture of isomers is usually called an enantiomeric mixture. A 50:50 mixture of enantiomers is called a racemic mixture or racemate, which may result in no stereoselectivity or stereospecificity during chemical reactions. The terms "racemic mixture" or "racemate" refers to an equimolar mixture of two enantiomers, lacking optical activity.

"Tautomer" or "tautomeric form" means that isomers of different energy structures can be converted into each other through a low energy barrier. For example, proton tautomers (that is, tautomers of proton shift) include interconversions through proton migration, such as keto-enol and imine-enamine isomerization. Atomic (valence) tautomers include the interconversion of recombined bond electrons. Unless otherwise indicated, the structural formula described in the present disclosure includes all isomeric forms (such as enantiomers, diastereomers and geometric isomers): for example, R and S configurations containing asymmetric centers, (Z), (E) isomers of double bonds, and (Z), (E) conformational isomers. Therefore, a single stereochemical isomer of the compound of the present disclosure or a mixture of its enantiomers, diastereomers or geometric isomers all fall into the scope of the present disclosure.

The "base" in the present disclosure refers to a Brønsted base or a Lewis base.

In the present disclosure, "chemical bond" particularly means a covalent bond.

"Pharmaceutically acceptable salt" refers to certain salts of the compound of the present disclosure that can maintain the original biological activity and are suitable for medical use. The pharmaceutically acceptable salt of the compound represented by formula (I) is an amine salt formed with a suitable acid, and the suitable acid includes inorganic acid and organic acid, such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid, etc.

"Pharmaceutical composition" means a mixture comprising one or more compounds described herein or their physiologically pharmaceutically acceptable salts or prodrugs and other chemical components, as well as other components such as physiologically pharmaceutically acceptable carriers and excipients. The purpose of the pharmaceutical composition is to promote the administration to an organism, facilitate the absorption of the active ingredients and then exert the biological activity.

Synthetic Method of the Compound of the Present Disclosure

In order to accomplish the purpose of the present disclosure, the present disclosure can be implemented by adopting the following technical solutions:

The compound of formula (I) of the present disclosure has the following three preparation methods according to the different groups:

Method 1:

When $R^3$ is $R^{3'}$, and $R3'$ is selected from hydrogen, cyano, $C_1$-$C_6$ alkyl, $C_1$-$C_3$ alkoxy, $C_3$-$C_6$ cycloalkyl, and —$R^9CO_2R^{10'}$, wherein the $C_1$-$C_6$ alkyl is optionally further substituted with one or more halogen atoms; alternatively, $R^2$, $R^{3'}$ and the two carbon atoms attached thereto together form an aryl group, which is optionally further substituted with one or more halogen atoms or C1-$C_6$ alkyl; $R^9$ is selected from a chemical bond and $C_1$-$C_4$ alkylene group; $R^{10'}$ is selected from $C_1$-$C_6$ alkyl; i.e., a compound of formula (I) is a compound of formula (I-a), which is obtained by the reaction of a compound of formula (B) or a salt thereof with a compound of formula (A) or a salt thereof under the action of a condensing agent:

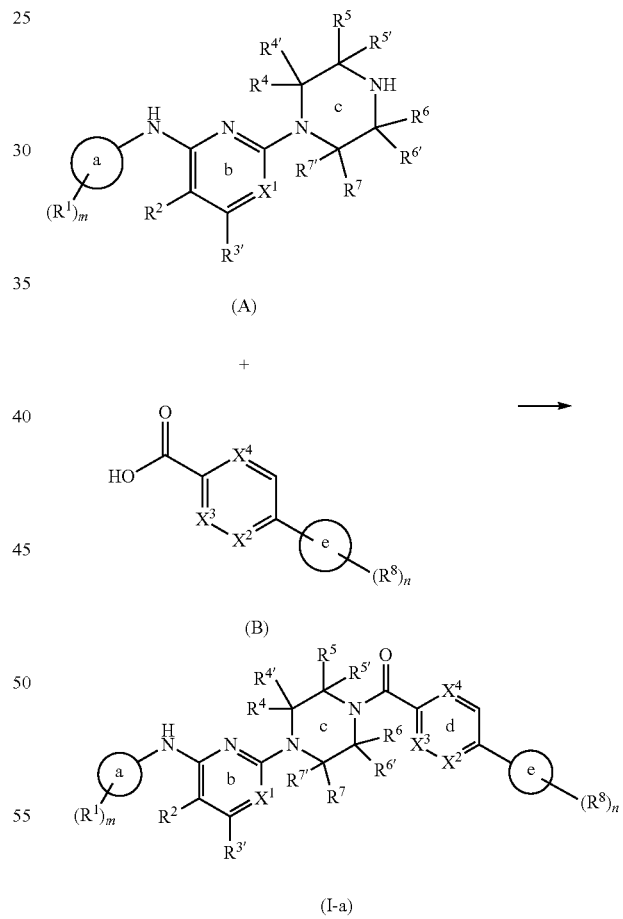

The reaction temperature of the above reaction is 0-40° C.; the reaction solvent is dichloromethane, acetonitrile or N,N-dimethylformamide, preferably N,N-dimethylformamide; the condensing agent is HATU, PyBOP or $T_3P$, Preferably HATU or PyBOP; the above reaction is carried out under basic conditions, and the base used is diisopropylethylamine or triethylamine, preferably diisopropylethylamine; wherein, ring a, ring e, $X^1$, $X^2$, $X^3$, $X^4$, $R^1$, $R^2$, $R^4$, $R^{4'}$, $R^5$, $R^{5'}$, $R^6$, $R^{6'}$, $R^7$, $R^{7'}$, $R^8$, m, and n have the same definitions as in formula (I).

Wherein, the preparation method of the compound represented by formula (A) is as follows:

First, when $X^1$ is N, the reaction steps include:

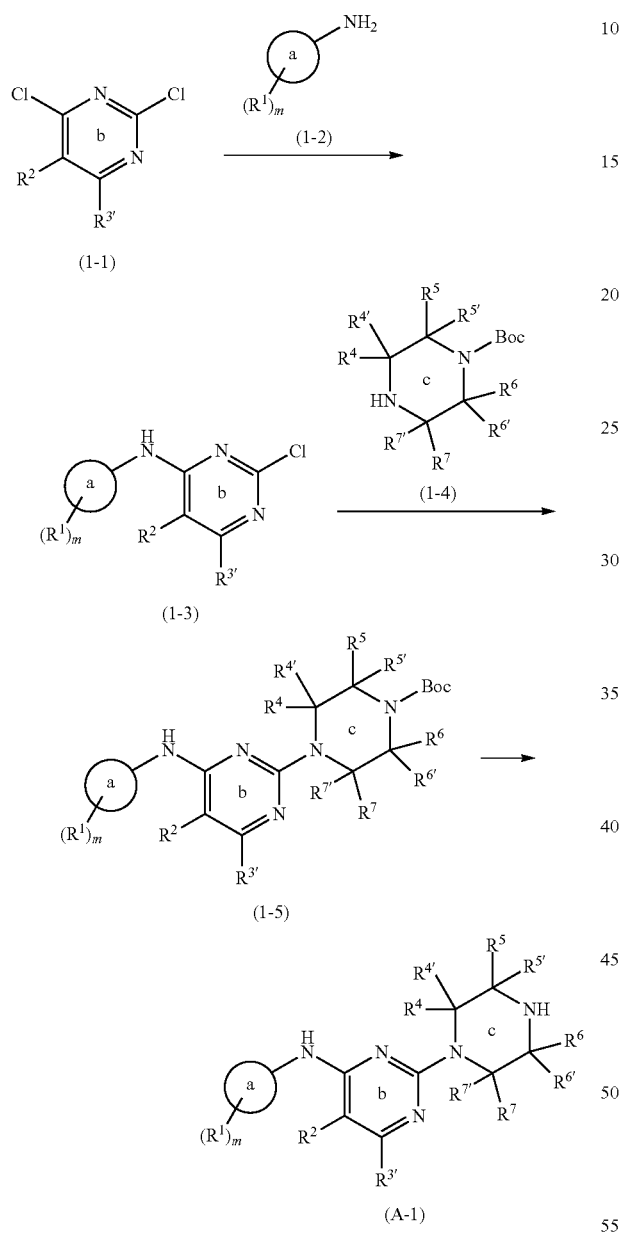

Second, when $X^1$ is CH, the reaction steps include:

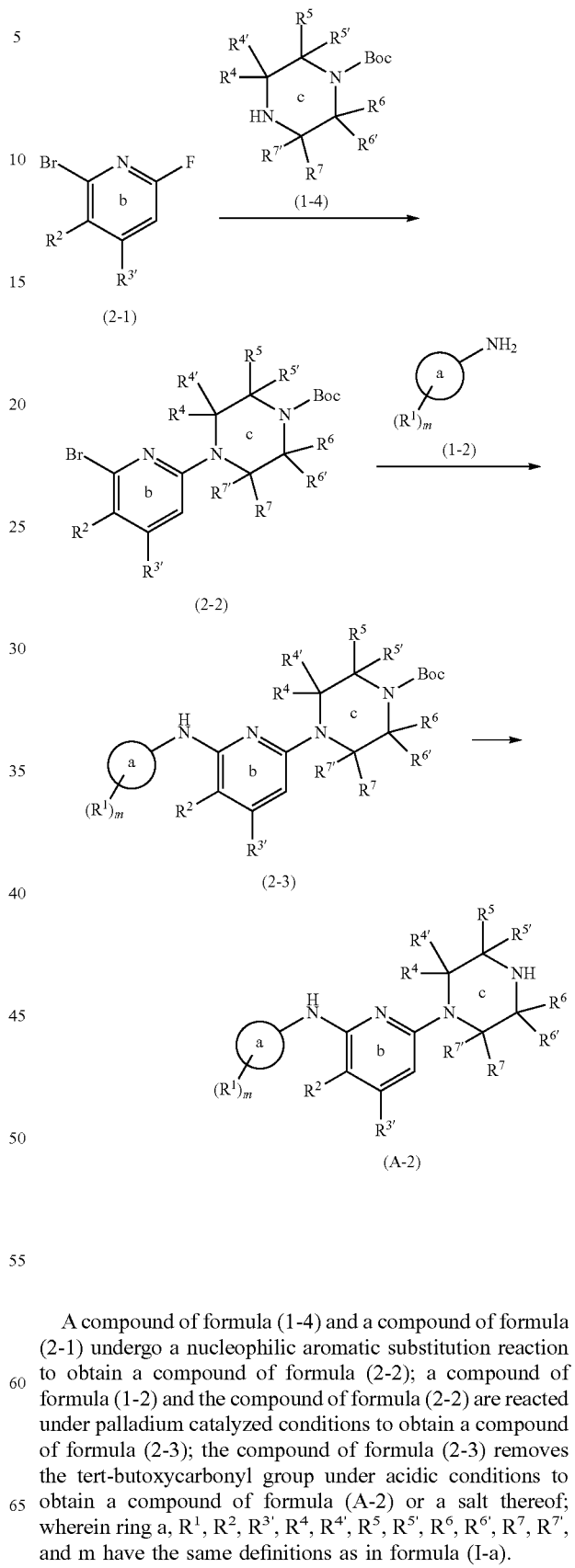

A compound of formula (1-2) and a compound of formula (1-1) undergo a nucleophilic aromatic substitution reaction to obtain a compound of formula (1-3); a compound of formula (1-4) and the compound of formula (1-3) undergo a nucleophilic aromatic substitution reaction to obtain a compound of formula (1-5); the compound of formula (1-5) removes the tert-butoxycarbonyl group under acidic conditions to obtain a compound of formula (A-1) or a salt thereof; wherein ring a, $R^1$, $R^2$, $R^{3'}$, $R^4$, $R^{4'}$, $R^5$, $R^{5'}$, $R^6$, $R^{6'}$, $R^7$, $R^{7'}$, and m have the same definitions as in formula (I-a).

A compound of formula (1-4) and a compound of formula (2-1) undergo a nucleophilic aromatic substitution reaction to obtain a compound of formula (2-2); a compound of formula (1-2) and the compound of formula (2-2) are reacted under palladium catalyzed conditions to obtain a compound of formula (2-3); the compound of formula (2-3) removes the tert-butoxycarbonyl group under acidic conditions to obtain a compound of formula (A-2) or a salt thereof; wherein ring a, $R^1$, $R^2$, $R^{3'}$, $R^4$, $R^{4'}$, $R^5$, $R^{5'}$, $R^6$, $R^{6'}$, $R^7$, $R^{7'}$, and m have the same definitions as in formula (I-a).

The preparation of the compound represented by formula (B) include two methods:

First, when ring e is attached via a N atom to ring d:

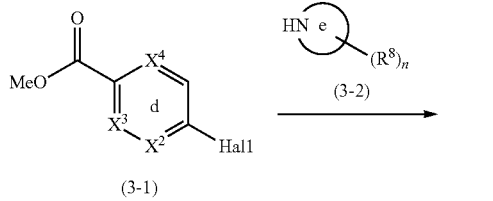

(3-1)

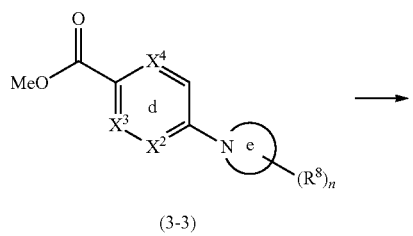

(3-3)

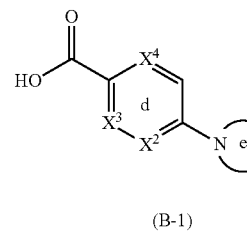

(B-1)

A compound of formula (3-2) and a compound of formula (3-1) undergo a nucleophilic aromatic substitution reaction to obtain a compound of formula (3-3); the compound of formula (3-3) is hydrolyzed to produce a compound of formula (B-1), wherein, Hal1 is fluorine, chlorine, bromine or iodine, and ring e, $X^2$, $X^3$, $X^4$, $R^8$ and n have the same definitions as in formula (I-a).

Second, when ring e is attached via a C atom to ring d:

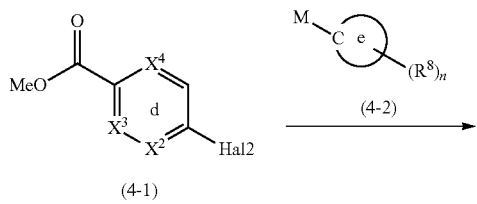

(4-1)

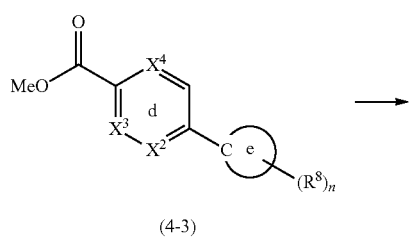

(4-3)

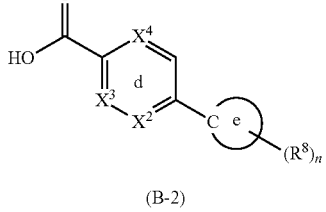

(B-2)

M is —$B(OH)_2$ or Bpin.

A compound of formula (4-2) and a compound of formula (4-1) undergo Suzuki coupling reaction to obtain a compound of formula (4-3); the compound of formula (4-3) is hydrolyzed to produce a compound of formula (B-2); wherein Hal2 is chlorine, bromine or iodine; and ring e, $X^2$, $X^3$, $X^4$, $R^8$ and n have the same definitions as in formula (I-a).

Method 2:

When $R^3$ is $R^9COOH$, a compound of formula (I) is a compound of formula (I-c), which is prepared by the reaction of a compound of formula (I-b) with a base (lithium hydroxide, sodium hydroxide or potassium hydroxide, etc.):

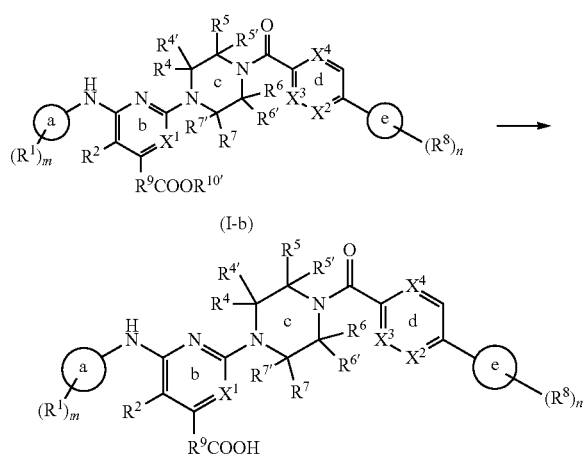

(I-b)

(I-c)

Wherein, $R^9$ is selected from a chemical bond and $C_1$-$C_4$ alkylene group; $R^{10'}$ is selected from $C_1$-$C_6$ alkyl; and ring a, ring e, $X^1$, $X^2$, $X^3$, $X^4$, $R^1$, $R^2$, $R^4$, $R^{4'}$, $R^5$, $R^{5'}$, $R^6$, $R^{6'}$, $R^7$, $R^{7'}$, $R^8$, m and n have the same definitions as in formula (I).

Method 3:

When $R^3$ is $R^{3'''}$, and $R^{3'''}$ is a $C_1$-$C_5$ primary alcohol group, a compound of formula (I) is a compound of formula (I-d), which is prepared by the reaction of a compound of formula (I-b) with a reducing reagent ($NaBH_4$, $LiAlH_4$, etc.):

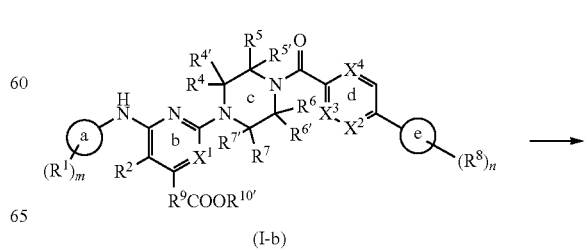

(I-b)

-continued

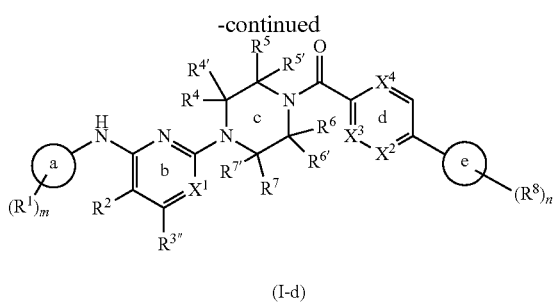

(I-d)

Wherein, $R^9$ is selected from a chemical bond and $C_1$-$C_4$ alkylene group; $R^{10'}$ is selected from $C_1$-$C_6$ alkyl; and ring a, ring e, $X^1$, $X^2$, $X^3$, $X^4$, $R^1$, $R^2$, $R^4$, $R^{4'}$, $R^5$, $R^{5'}$, $R^6$, $R^{6'}$, $R^7$, $R^{7'}$, $R^8$, m and n have the same definitions as in formula (I).

Method 4:

When $R^3$ is $R^{3''''}$, and $R^{3''''}$ is a $C_3$-$C_7$ tertiary alcohol group, a compound of formula (I) is a compound of formula (I-e), which is prepared by the reaction of a compound of formula (I-b) with methylmagnesium iodide or methylmagnesium bromide:

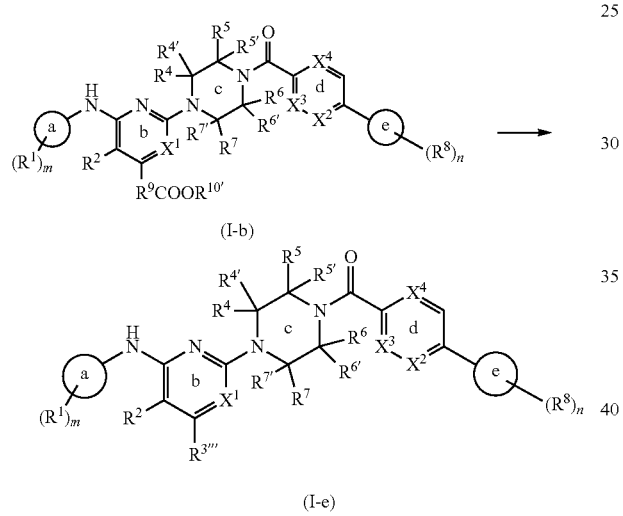

Wherein, $R^9$ is selected from a chemical bond and $C_1$-$C_4$ alkylene group; $R^{10'}$ is selected from $C_1$-$C_6$ alkyl; and ring a, ring e, $X^1$, $X^2$, $X^3$, $X^4$, $R^1$, $R^2$, $R^4$, $R^{4'}$, $R^5$, $R^{5'}$, $R^6$, $R^{6'}$, $R^7$, $R^{7'}$, $R^8$, m and n have the same definitions as in formula (I).

DETAILED DESCRIPTION

Examples

The examples show the preparation and related structure identification data of specific compounds of the present disclosure. It must be noted that the following examples are used to illustrate the present disclosure but not to limit the present disclosure. The structure of the compound was determined by nuclear magnetic resonance (NMR) and mass spectrometry (MS). $^1$H NMR spectrum was measured with a Bruker instrument (400 MHz), with chemical shift expressed in ppm, and tetramethylsilane as internal standard (0.00 ppm). Expressions in $^1$H NMR include: s=singlet, d=doublet, m=multiplet, br=broad, dd=doublet of doublet, dt=doublet of triplet. If the coupling constant is provided, the unit is Hz. FINNIGAN LCQAd (ESI) mass spectrometer (manufacturer: Thermo, model: Finnigan LCQ advantage MAX) was used for mass spectrometry.

The thin layer chromatography silica gel plate used were Yantai Huanghai $HSGF_{254}$ or Qingdao $GF_{254}$ silica gel plate, the size of the silica gel plate used in thin layer chromatography (TLC) is 0.15 mm~0.2 mm, and the size used for thin layer chromatography separation and product purification is 0.4 mm~0.5 mm silica gel preparation plate.

Silica gel column chromatography generally adopted Yantai Huanghai 200~300 mesh silica gel as the carrier.

The known starting materials of the present disclosure can be synthesized by or according to methods known in the art, or can be purchased from companies such as ABCR GmbH & Co. KG, Acros Organnics, Aldrich Chemical Company, Accela ChemBio Inc, Chembee Chemicals, and Bidepharm.

Unless otherwise specified in the examples, the reactions were all carried out under an air atmosphere.

Nitrogen atmosphere means that the reaction flask was connected to a nitrogen balloon with a volume of about 1 L.

Unless otherwise specified in the examples, the solution in the reaction refers to an aqueous solution.

Unless otherwise specified in the examples, the reaction temperature was room temperature, and the range of room temperature was 20° C.~30° C.

The monitoring of the reaction progress in the examples adopted thin layer chromatography (TLC). The developing solvent systems used were: dichloromethane and methanol system, n-hexane and ethyl acetate system. The volume ratio of the developing solvent was adjusted according to the polarity of the compound.

Example 1

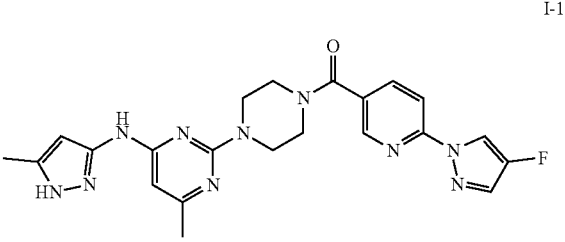 [SMILES: Cc1cc(Nc2cc(C)[nH]n2)nc(N2CCN(C(=O)c3ccc(-n4cc(F)cn4)nc3)CC2)n1]

I-1

Step 1: Synthesis of 2-chloro-6-methyl-N-(5-methyl-1H-pyrazol-3-yl)pyrimidin-4-amine

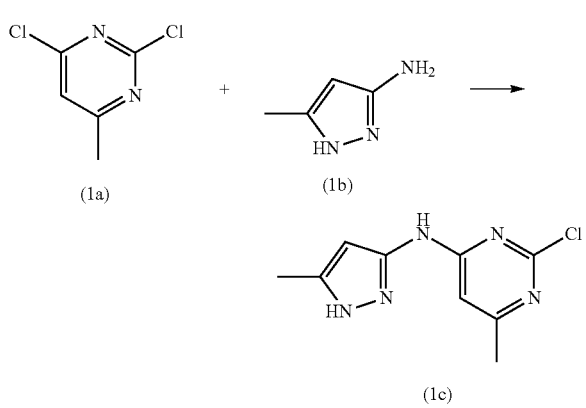

6-methyl-2,4-dichloropyrimidine (1a) (9.72 g, 60 mmol), 5-methyl-1H-3-aminopyrazole (1b) (7.0 g, 72 mmol) and DIPEA (11.6 g, 72 mmol) were dissolved in 30 mL DMSO, and reacted at 60° C. with stirring. After the raw materials in the reaction monitored by TLC disappeared, the temperature was reduced to room temperature, and 10 mL of water was added to quench the reaction. Then 200 mL of ethyl acetate was added. The organic phase was washed with water three times (30 mL×3), followed by saturated brine once, dried over anhydrous sodium sulfate, and filtered, and the solvent was removed under reduced pressure to obtain a brown-yellow viscous liquid, which was added with 80 mL of dichloromethane to dissolve and let stand for 3 hours. 9.9 g of a white solid 2-chloro-6-methyl-N-(5-methyl-1H-pyrazol-3-yl)pyrimidin-4-amine (1c) was precipitated, with a yield of 74%.

MS m/z (ESI): 224.3 [M+1]

Step 2: Synthesis of tert-butyl 4-(4-methyl-6-((5-methyl-1H-pyrazol-3-yl)amino)pyrimidin-2-yl)piperazine-1-carboxylate

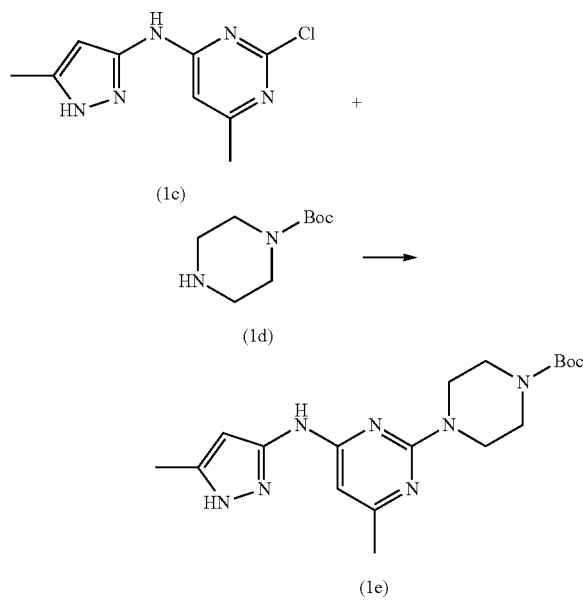

2-chloro-6-methyl-N-(5-methyl-1H-pyrazol-3-yl)pyrimidin-4-amine (1c) (892 mg, 4 mmol), 1-tert-butoxycarbonylpiperazine (1d) (1.49 g, 8 mmol) and K₂CO₃ (1.66 g, 12 mmol) were dissolved in 25 mL DMF and reacted at 140° C. for 6 hours. The reaction solution was cooled to room temperature, and 10 mL water was added to quench the reaction. Then 150 mL of ethyl acetate was added. The organic phase was washed with water (15 mL×3) three times, followed by saturated brine once, dried over anhydrous sodium sulfate, and filtered, and the solvent was removed under reduced pressure. After separation by silica gel column chromatography (the eluent and volume ratio: dichloromethane:methanol=20:1), 1.01 g of tert-butyl 4-(4-methyl-6-((5-methyl-1H-pyrazol-3-yl)amino)pyrimidin-2-yl)piperazine-1-carboxylate (1e) was obtained, with a yield of 67%.

MS m/z (ESI): 374.2 [M+1]

Step 3: Synthesis of 6-methyl-N-(5-methyl-1H-pyrazol-3-yl)-2-(1-piperazinyl)pyrimidin-4-amine Hydrochloride

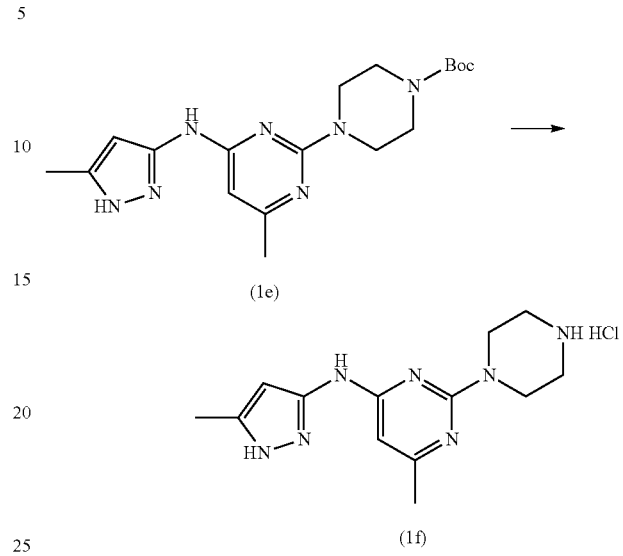

Tert-butyl 4-(4-methyl-6-((5-methyl-1H-pyrazol-3-yl)amino)pyrimidin-2-yl)piperazine-1-carboxylate (1e) (1.24 g, 3.3 mmol) was dissolved in 25 mL of 1,4-dioxane, 25 mL of HCl/1,4-dioxane solution at a concentration of 2.6 mol/L was added dropwise, and reacted at 50° C. for 4 hours. After the completion of reaction, the filtration was performed, and the filter cake was washed with ethyl acetate followed by ethyl ether, and dried under vacuum to obtain 1.1 g of a pale yellow solid 6-methyl-N-(5-methyl-1H-pyrazol-3-yl)-2-(1-piperazinyl)pyrimidin-4-amine hydrochloride (1f), with a yield of >99%.

MS m/z (ESI): 274.2 [M+1]

Step 4: Synthesis of methyl 6-(4-fluoro-1H-pyrazol-1-yl)nicotinate

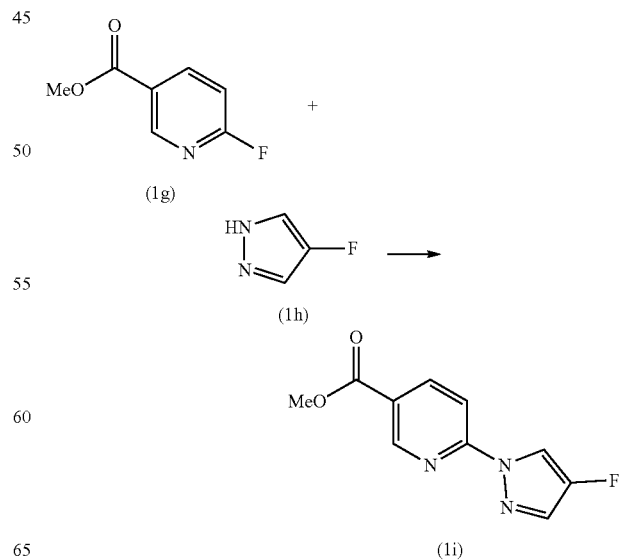

Methyl 6-fluoronicotinate (1g) (3.10 g, 20 mmol), 4-fluoropyrazole (1h) (2.07 g, 24 mmol) and K$_2$CO$_3$ (6.91 g, 50 mmol) were dissolved in 25 mL DMF, and reacted at 100° C. for 6 hours. The reaction solution was cooled to room temperature, and 10 mL water was added to quench the reaction. Then 150 mL of ethyl acetate was added. The organic phase was washed with water (15 mL×3) three times, followed by saturated brine once, dried over anhydrous sodium sulfate, and filtered, and the solvent was removed under reduced pressure. After separation by silica gel column chromatography (the eluent and volume ratio: dichloromethane:methanol=20:1), 3.6 g of methyl 6-(4-fluoro-1H-pyrazol-1-yl)nicotinate (1i) was obtained, with a yield of 82%.

MS m/z (ESI): 222.1 [M+1]

Step 5: Synthesis of
6-(4-fluoro-1H-pyrazol-1-yl)nicotinic Acid

Methyl 6-(4-fluoro-1H-pyrazol-1-yl)nicotinate (1i) (3.6 g, 16.2 mmol) and lithium hydroxide monohydrate (1.36 g, 32.4 mmol) were dissolved in a mixed solvent prepared with 40 mL methanol and 20 mL distilled water, and reacted at 50° C. for 2 hours. After the raw materials in the reaction monitored by TLC disappeared, the reaction solution was cooled to room temperature. After the solvent was removed under reduced pressure, 100 mL of distilled water was added, and 1 mol/L dilute hydrochloric acid was added to adjust the pH value to 2-5. The mixture was stirred for 1 hour and filtered, and the filter cake was dried at 50° C. to obtain 3.1 g of 6-(4-fluoro-1H-pyrazol-1-yl)nicotinic acid (1j), with a yield of 92%.

MS m/z (ESI): 208.1 [M+1]

Step 6: Synthesis of (6-(4-fluoro-1H-pyrazol-1-yl)pyridin-3-yl)(4-(4-methyl-6-((5-methyl-1H-pyrazol-3-yl)amino)pyrimidin-2-yl)piperazin-1-yl)methanone

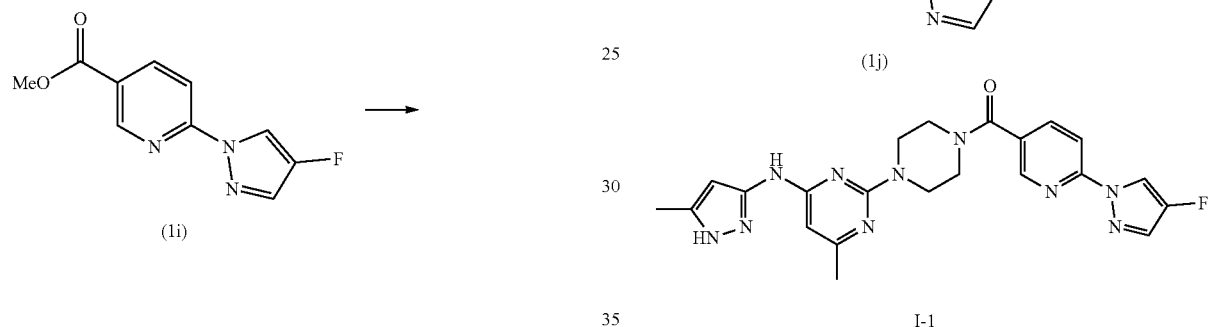

6-(4-fluoro-1H-pyrazol-1-yl)nicotinic acid (1j) (83 mg, 0.4 mmol) and HATU (228 mg, 0.6 mmol) were dissolved in 4 mL DMF and cooled to 0° C. DIPEA (163 mg, 1.6 mmol) was added and stirred for 2 minutes before 6-methyl-N-(5-methyl-1H-pyrazol-3-yl)-2-(1-piperazinyl)pyrimidin-4-amine hydrochloride (1f) (140 mg, 0.45 mmol) was added. The reaction was kept at 0° C. for 30 minutes, and 10 mL of water was added to quench the reaction. Then 100 mL of ethyl acetate was added. The organic phase was washed with water (15 mL×3) three times, followed by saturated brine once, dried over anhydrous sodium sulfate, and filtered, and the solvent was removed under reduced pressure. After separation by silica gel column chromatography (the eluent and volume ratio: dichloromethane:methanol=30:1), a crude product was obtained and further separated by silica gel preparation plate (the developing solvent and volume ratio: dichloromethane:methanol=10:1) to obtain 80 mg of (6-(4-fluoro-1H-pyrazol-1-yl)pyridin-3-yl)(4-(4-methyl-6-((5-methyl-1H-pyrazol-3-yl)amino)pyrimidin-2-yl)piperazin-1-yl)methanone (I-1), with a yield of 43%.

$^1$H NMR (400 MHz, DMSO-d$_6$) δ 11.81 (s, 1H), 9.28 (s, 1H), 8.76 (d, J=4.5 Hz, 1H), 8.57 (s, 1H), 8.09 (d, J=8.2 Hz, 1H), 7.99 (t, J=7.2 Hz, 2H), 6.24 (s, 1H), 6.11 (s, 1H), 3.81-3.73 (m, 6H), 3.51-3.46 (m, 2H), 2.18 (s, 3H), 2.13 (s, 3H) ppm.

MS m/z (ESI): 463.2 [M+1].

With reference to Example 1, the following compounds can be prepared:

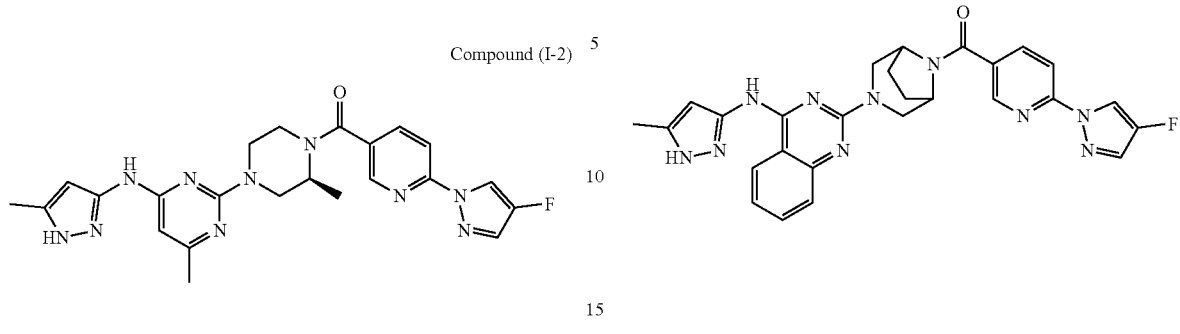

Compound (I-2)

¹H NMR (400 MHz, DMSO-d₆) δ 11.80 (s, 1H), 9.26 (s, 1H), 8.74 (d, J=4.6 Hz, 1H), 8.55 (s, 1H), 8.07 (d, J=8.5 Hz, 1H), 7.99-7.97 (m, 2H), 6.22 (s, 1H), 6.11 (s, 1H), 4.52-4.49 (s, 2H), 3.17-2.94 (s, 3H), 2.18 (s, 3H), 2.12 (s, 3H), 1.19 (d, J=6.8 Hz, 3H) ppm.

MS m/z (ESI): 477.2 [M+1].

Compound (I-3)

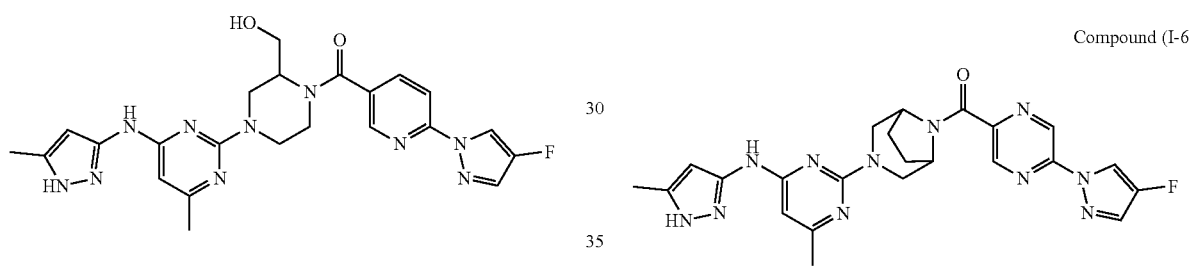

¹H NMR (400 MHz, DMSO-d₆) δ 11.84 (s, 1H), 9.29 (s, 1H), 8.75 (d, J=4.5 Hz, 1H), 8.57 (s, 1H), 8.09 (d, J=8.5 Hz, 1H), 8.02-7.93 (m, 2H), 6.21 (s, 1H), 6.14 (s, 1H), 5.01-4.21 (m, 4H), 3.65-3.35 (m, 3H), 3.14-2.84 (m, 3H), 2.18 (s, 3H), 2.12 (s, 3H) ppm.

MS m/z (ESI): 493.2 [M+1].

Compound (I-4)

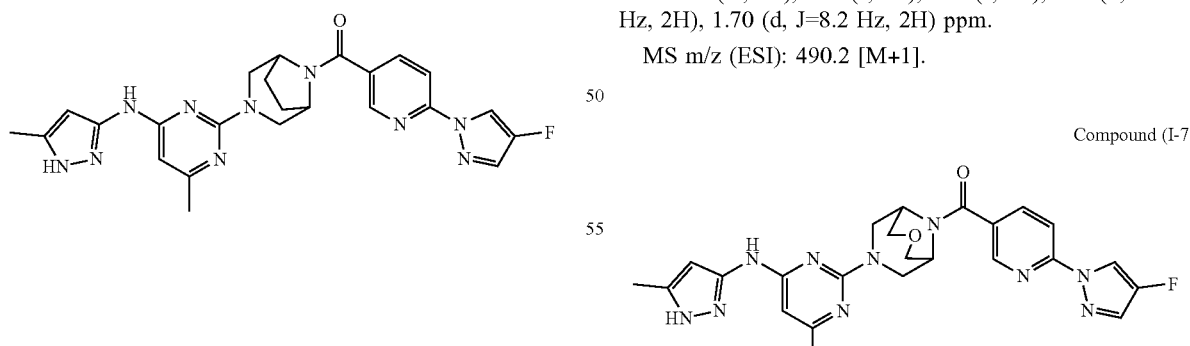

¹H NMR (400 MHz, DMSO-d₆) δ 11.81 (s, 1H), 9.27 (s, 1H), 8.76 (d, J=4.4 Hz, 1H), 8.64 (s, 1H), 8.17 (d, J=8.5 Hz, 1H), 8.02-7.98 (m, 2H), 6.23 (s, 1H), 6.12 (s, 1H), 4.81-4.79 (m, 1H), 4.50-4.37 (m, 2H), 4.21-4.18 (m, 1H), 3.13-3.09 (m, 2H), 2.19 (s, 3H), 2.12 (s, 3H), 1.95-1.83 (m, 2H), 1.71-1.61 (m, 2H) ppm.

MS m/z (ESI): 489.2 [M+1].

Compound (I-5)

¹H NMR (400 MHz, DMSO-d₆) δ 12.12 (s, 1H), 10.03 (s, 1H), 8.77 (d, J=4.5 Hz, 1H), 8.66 (s, 1H), 8.38 (d, J=8.2 Hz, 1H), 8.23-8.07 (m, 1H), 8.06-7.90 (m, 2H), 7.56 (t, J=7.7 Hz, 1H), 7.33 (d, J=8.4 Hz, 1H), 7.11 (t, J=7.6 Hz, 1H), 6.44 (s, 1H), 4.84 (s, 1H), 4.74-4.38 (m, 2H), 4.24 (s, 1H), 3.23-3.20 (m, 2H), 2.26 (s, 3H), 1.91 (s, 2H), 1.71-1.68 (m, 2H) ppm.

MS m/z (ESI): 525.2 [M+1].

Compound (I-6)

¹H NMR (400 MHz, DMSO-d₆) δ 11.85 (s, 1H), 9.26-9.22 (m, 2H), 8.88 (s, 1H), 8.82 (d, J=4.5 Hz, 1H), 8.13 (d, J=4.0 Hz, 1H), 6.23 (s, 1H), 6.12 (s, 1H), 4.86-4.85 (m, 1H), 4.81-4.65 (m, 1H), 4.52-4.50 (m, 1H), 4.42-4.39 (m, 1H), 3.17-3.08 (m, 2H), 2.20 (s, 3H), 2.12 (s, 3H), 1.91 (d, J=11.7 Hz, 2H), 1.70 (d, J=8.2 Hz, 2H) ppm.

MS m/z (ESI): 490.2 [M+1].

Compound (I-7)

¹H NMR (400 MHz, DMSO-d₆) δ 9.22 (s, 1H), 8.77 (d, J=4.5 Hz, 1H), 8.62 (s, 1H), 8.14 (s, 2H), 8.01 (t, J=7.0 Hz, 2H), 6.15 (brs, 2H), 5.09-4.41 (m, 3H), 4.20-3.63 (m, 5H), 3.25-3.17 (m, 2H), 2.18 (s, 3H), 2.12 (s, 3H) ppm.

MS m/z (ESI): 505.5 [M+1]

Compound (I-8)

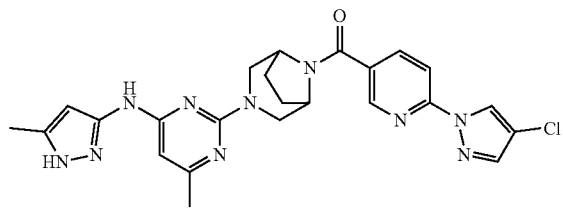

$^1$H NMR (400 MHz, DMSO-d$_6$) δ 11.83 (s, 1H), 9.25 (s, 1H), 8.86 (s, 1H), 8.65 (s, 1H), 8.19 (d, J=8.7 Hz, 1H), 8.03 (s, 1H), 8.01-7.94 (m, 1H), 6.23 (s, 1H), 6.12 (s, 1H), 4.86-4.75 (m, 1H), 4.52-4.35 (m, 2H), 4.23-4.17 (m, 1H), 3.14-3.06 (m, 2H), 2.19 (s, 3H), 2.12 (s, 3H), 1.96-1.83 (m, 2H), 1.75-1.62 (m, 2H) ppm.

MS m/z (ESI): 505.2 [M+1].

Compound (I-9)

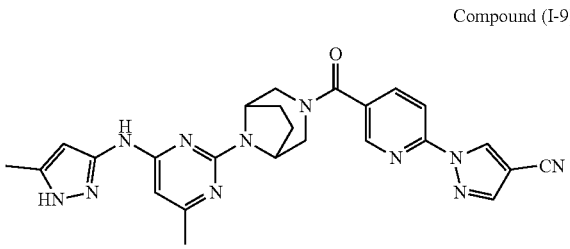

$^1$H NMR (400 MHz, DMSO-d6) δ 11.84 (s, 1H), 9.48 (s, 1H), 9.28 (s, 1H), 8.71 (s, 1H), 8.48 (s, 1H), 8.24 (s, 1H), 8.06 (s, 1H), 6.23 (s, 1H), 6.11 (s, 1H), 4.81 (s, 1H), 4.49 (s, 1H), 4.38 (s, 1H), 4.19 (s, 1H), 3.33 (s, 2H), 2.19 (s, 3H), 2.11 (s, 3H), 1.90 (s, 2H), 1.66 (s, 2H) ppm.

MS m/z (ESI): 496.2 [M+1].

Compound (I-10)

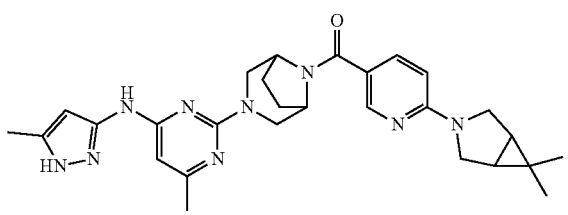

$^1$H NMR (400 MHz, DMSO-d$_6$) δ 11.82 (s, 1H), 9.27 (s, 1H), 8.30 (d, J=2.5 Hz, 1H), 7.67 (dd, J=8.7, 2.3 Hz, 1H), 6.43 (d, J=8.7 Hz, 1H), 6.21 (s, 1H), 6.13 (s, 1H), 4.43-4.8 (m, 3H), 3.65-3.20 (m, 5H), 3.07 (d, J=12.6 Hz, 2H), 2.20 (s, 3H), 2.11 (s, 3H), 1.89-1.40 (m, 6H), 1.06 (s, 3H), 0.83 (s, 3H) ppm.

MS m/z (ESI): 514.3 [M+1]

Compound (I-11)

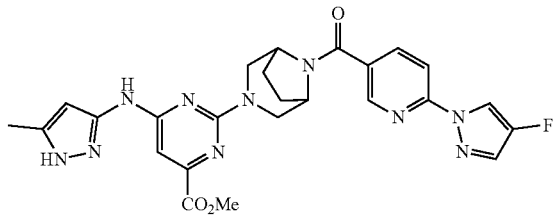

$^1$H NMR (400 MHz, DMSO-d$_6$) δ 12.00 (s, 1H), 9.90 (s, 1H), 8.76 (d, J=4.4 Hz, 1H), 8.65 (d, J=2.0 Hz, 1H), 8.18 (dd, J=8.5, 2.2 Hz, 1H), 8.09-7.89 (m, 2H), 6.80 (s, 1H), 6.29 (s, 1H), 4.83 (s, 1H), 4.49-4.35 (m, 2H), 4.24 (s, 1H), 3.81 (s, 3H), 3.22-3.15 (m, 2H), 2.21 (s, 3H), 1.91 (s, 2H), 1.83-1.61 (m, 2H) ppm.

MS m/z (ESI): 533.2 [M+1]

Compound (I-12)

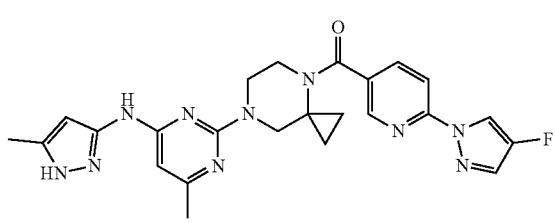

MS m/z (ESI): 489.2 [M+1]

Example 2

(I-13)

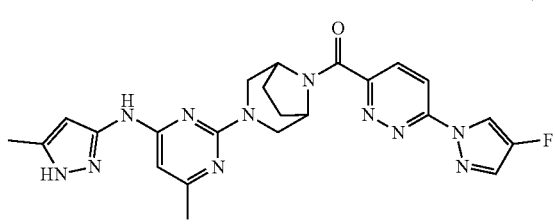

Step 1: Synthesis of tert-butyl 3-(4-methyl-6-((5-methyl-1H-pyrazol-3-yl)amino)pyrimidin-2-yl)-3,8-diazabicyclo[3.2.1]octane-8-carboxylate

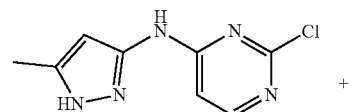

(1c)

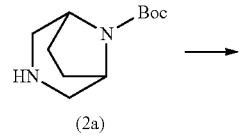

(2a)

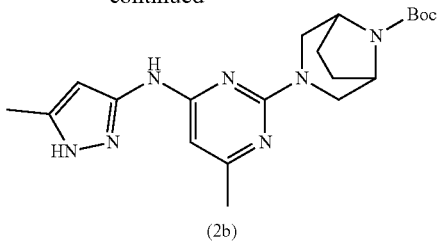

(2b)

2-chloro-6-methyl-N-(5-methyl-1H-pyrazol-3-yl)pyrimidin-4-amine (1c) (2.01 g, 9 mmol), tert-butyl 3,8-diazabicyclo[3.2.1]octane-8-carboxylate (2a) (3.82 g, 18 mmol) and K₂CO₃ (3.73 g, 27 mmol) were dissolved in 25 mL DMAc, and reacted at 140° C. After the reaction monitored by TLC completed, the reaction solution was cooled to room temperature, and 5 mL of water was added to quench the reaction. Then 150 mL of ethyl acetate was added. The organic phase was washed with water (15 mL×3) three times, followed by saturated brine once, dried over anhydrous sodium sulfate, and filtered, and the solvent was removed under reduced pressure.

After separation by silica gel column chromatography (the eluent and volume ratio: dichloromethane:methanol=20:1), 2.81 g of tert-butyl 3-(4-methyl-6-((5-methyl-1H-pyrazol-3-yl)amino)pyrimidin-2-yl)-3, 8-diazabicyclo[3.2.1]octane-8-carboxylate (2b) was obtained, with a yield of 77%.

MS m/z (ESI): 400.5 [M+1]

Step 2: Synthesis of 2-(3,8-diazabicyclo[3.2.1]octane-3-yl)-6-methyl-N-(5-methyl-1H-pyrazol-3-yl)pyrimidin-4-amine Hydrochloride

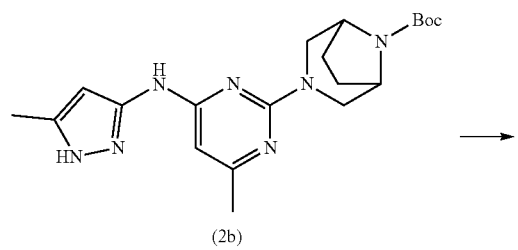

Tert-butyl 3-(4-methyl-6-((5-methyl-1H-pyrazol-3-yl)amino)pyrimidin-2-yl)-3,8-diazabicyclo[3.2.1]octane-8-carboxylate (2b) (2.6 g, 6.5 mmol) was dissolved in 40 mL of 1,4-dioxane, 40 mL of HCl/1,4-dioxane at a concentration of 2.6 mol/L was added dropwise, and reacted at 50° C. for 4 hours. The filtration was then performed, and the filter cake was washed with ethyl acetate followed by ethyl ether, and dried under vacuum to obtain 2.2 g of 2-(3,8-diazabicyclo[3.2.1]octane-3-yl)-6-methyl-N-(5-methyl-1H-pyrazol-3-yl)pyrimidin-4-amine hydrochloride (2c), with a yield of >99%.

MS m/z (ESI): 300.3 [M+1]

Step 3: Synthesis of methyl 6-(4-fluoro-1H-pyrazol-1-yl)pyridazin-3-carboxylate

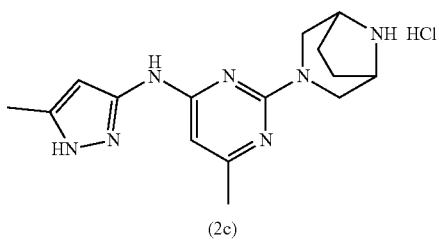

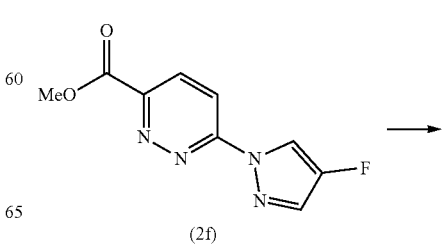

4-fluoro-1H-pyrazole (1h) (2.4 g, 27.8 mmol) was dissolved in 40 mL DMF and cooled to 0° C. Sodium hydride (1.4 g, 34.8 mmol) was slowly added and reacted at 0° C. for 30 min before methyl 6-chloro-pyridazin-3-carboxylate (2d) (4.0 g, 23.2 mmol) was added. After the raw materials in the reaction monitored by TLC disappeared, 10 mL of ice water was added to quench the reaction. Then 200 mL of ethyl acetate was added. The organic phase was washed with water (30 mL×3) three times, followed by saturated brine once, dried over anhydrous sodium sulfate, and filtered, and the solvent was removed under reduced pressure. After separation by silica gel column chromatography (the eluents and volume ratio: dichloromethane:methanol=20:1), 4.53 g of methyl 6-(4-fluoro-1H-pyrazol-1-yl)pyridazin-3-carboxylate (2f) was obtained, with a yield of 88%.

MS m/z (ESI): 223.2 [M+1]

Step 4: Synthesis of 6-(4-fluoro-1H-pyrazol-1-yl)pyridazin-3-formic Acid

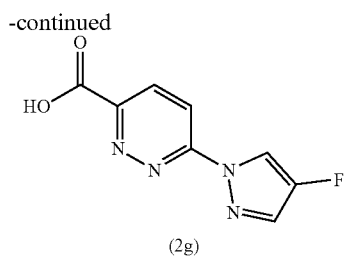

(2g)

Methyl 6-(4-fluoro-1H-pyrazol-1-yl)pyridazin-3-carboxylate (2f) (4.53 g, 20.4 mmol), lithium hydroxide monohydrate (1.71 g, 40.8 mmol) and 20 mL of distilled water were dissolved in 50 mL methanol and reacted at 40° C. for 2 hours. After the raw materials in the reaction monitored by TLC disappeared, the reaction solution was cooled to room temperature. After methanol was removed under reduced pressure, 100 mL of distilled water was added, and 1 mol/L dilute hydrochloric acid was added to adjust the pH value to 2-5. The mixture was stirred for 1 hour and filtered, and the filter cake was dried at 50° C. to obtain 3.81 g of 6-(4-fluoro-1H-pyrazol-1-yl)pyridazin-3-formic acid (2g), with a yield of 90%.

MS m/z (ESI): 209.1 [M+1]

Step 5: Synthesis of (6-(4-fluoro-1H-pyrazol-1-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone

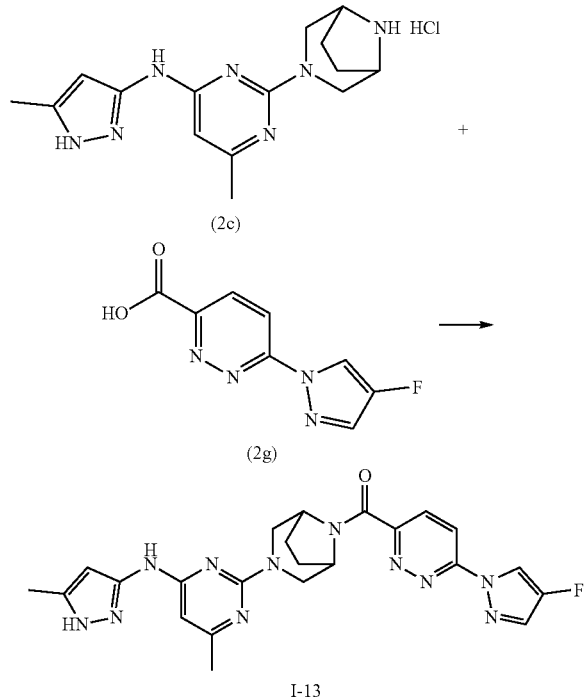

2-(3,8-diazabicyclo[3.2.1]octane-3-yl)-6-methyl-N-(5-methyl-1H-pyrazol-3-yl)pyrimidin-4-amine hydrochloride (2c) (700 mg, 2.1 mmol), 6-(4-fluoro-1H-pyrazol-1-yl)pyridazin-3-formic acid (2g) (390 mg, 1.9 mmol) and PyBOP (1.63 g, 3.1 mmol) were dissolved in 20 mL DMF and cooled to 0° C. before DIPEA (810 mg, 6.3 mmol) was added. The reaction was kept at 0° C. for 30 minutes, and 10 mL of water was added to quench the reaction. Then 150 mL of ethyl acetate was added. The organic phase was washed with water (20 mL×3) three times, followed by saturated brine once, dried over anhydrous sodium sulfate, and filtered, and the solvent was removed under reduced pressure. After separation by silica gel column chromatography (the eluent and volume ratio: dichloromethane:methanol=20:1), a crude product was obtained and further separated by silica gel preparation plate (the developing solvent and volume ratio: dichloromethane:methanol=10:1) to obtain 400 mg of (6-(4-fluoro-1H-pyrazol-1-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone (I-13), with a yield of 43%.

$^1$H NMR (400 MHz, DMSO-$d_6$) δ 11.85 (s, 1H), 9.27 (s, 1H), 9.08 (d, J=4.4 Hz, 1H), 8.34 (d, J=9.1 Hz, 1H), 8.21 (d, J=9.2 Hz, 1H), 8.15 (d, J=4.0 Hz, 1H), 6.19 (s, 1H), 6.14 (s, 1H), 4.89 (d, J=5.6 Hz, 1H), 4.74 (d, J=5.4 Hz, 1H), 4.55 (d, J=12.8 Hz, 1H), 4.43 (d, J=12.6 Hz, 1H), 3.20 (d, J=12.7 Hz, 1H), 3.12 (d, J=12.6 Hz, 1H), 2.20 (s, 3H), 2.12 (s, 3H), 1.92 (d, J=9.3 Hz, 2H), 1.71 (d, J=9.0 Hz, 2H) ppm.

MS m/z (ESI): 490.2 [M+1].

With reference to Example 2, the following compounds can be prepared:

Compound (I-14)

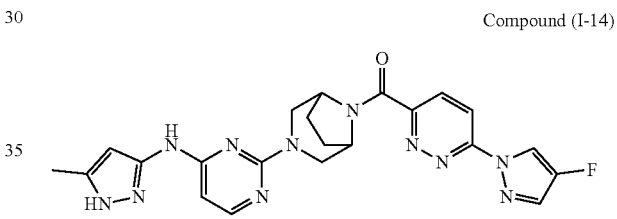

$^1$H NMR (400 MHz, DMSO-$d_6$) δ 11.89 (s, 1H), 9.42 (s, 1H), 9.09 (d, J=4.5 Hz, 1H), 8.35 (d, J=9.1 Hz, 1H), 8.22 (d, J=9.2 Hz, 1H), 8.15 (d, J=4.1 Hz, 1H), 7.89 (d, J=5.7 Hz, 1H), 6.33 (s, 1H), 6.16 (s, 1H), 4.95-4.84 (m, 1H), 4.84-4.69 (m, 1H), 4.54 (d, J=12.7 Hz, 1H), 4.43 (d, J=12.5 Hz, 1H), 3.21 (d, J=12.5 Hz, 1H), 3.17-3.08 (m, 1H), 2.21 (s, 3H), 1.93 (d, J=9.1 Hz, 2H), 1.71 (d, J=8.5 Hz, 2H) ppm.

MS m/z (ESI): 476.3

Compound (I-15)

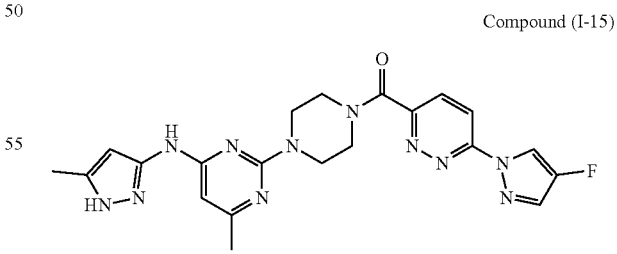

$^1$H NMR (400 MHz, DMSO-$d_6$) δ 11.86 (s, 1H), 9.30 (s, 1H), 9.05 (d, J=4.4 Hz, 1H), 8.34 (d, J=9.1 Hz, 1H), 8.14 (d, J=3.9 Hz, 1H), 8.12 (d, J=9.2 Hz, 1H), 6.24 (s, 1H), 6.12 (s, 1H), 3.86 (s, 2H), 3.78 (s, 2H), 3.75 (s, 2H), 3.59 (s, 2H), 2.18 (s, 3H), 2.13 (s, 3H) ppm.

MS m/z (ESI): 464.2 [M+1].

Compound (I-16)

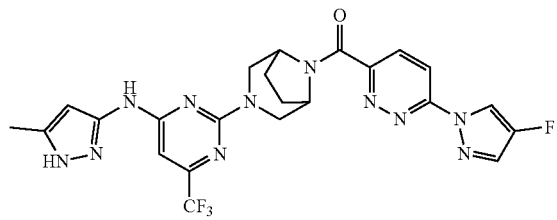

¹H NMR (400 MHz, DMSO-d₆) δ 12.06 (s, 1H), 10.10 (s, 1H), 9.08 (d, J=4.4 Hz, 1H), 8.35 (d, J=9.1 Hz, 1H), 8.22 (d, J=9.2 Hz, 1H), 8.15 (d, J=4.0 Hz, 1H), 6.59-6.26 (brs, 2H), 4.93 (s, 1H), 4.79 (s, 1H), 4.63-4.27 (m, 2H), 3.26-3.14 (m, 2H), 2.23 (s, 3H), 2.07-1.81 (m, 2H), 1.71 (d, J=8.7 Hz, 2H) ppm.

MS m/z (ESI): 544.2 [M+1].

Compound (I-17)

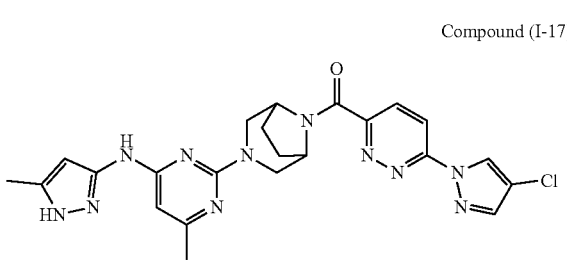 [SMILES: Cc1cc(Nc2cc(C)[nH]n2)nc(N2CC3CCC(C2)N3C(=O)c2cnc(-n3cc(F)cn3)cn2)n1]

¹H NMR (400 MHz, DMSO-d₆) δ 11.86 (s, 1H), 9.30 (s, 1H), 9.18 (s, 1H), 8.34 (d, J=9.1 Hz, 1H), 8.23 (d, J=9.1 Hz, 1H), 8.16 (s, 1H), 6.20 (s, 1H), 6.14 (s, 1H), 4.89 (s, 1H), 4.74 (s, 1H), 4.55 (d, J=11.7 Hz, 1H), 4.43 (d, J=12.2 Hz, 1H), 3.28-3.08 (m, 2H), 2.20 (s, 3H), 2.13 (s, 3H), 1.93 (d, J=8.8 Hz, 2H), 1.74-1.72 (m, 2H) ppm.

MS m/z (ESI): 506.2 [M+1].

Compound (I-18)

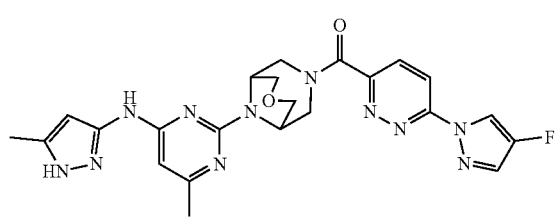

¹H NMR (400 MHz, DMSO-d₆) δ 11.82 (s, 1H), 9.22 (s, 1H), 9.07 (d, J=4.4 Hz, 1H), 8.36 (d, J=9.2 Hz, 1H), 8.19 (d, J=9.0 Hz, 1H), 8.15 (d, J=4.0 Hz, 1H), 6.16 (brs, 2H), 4.94 (s, 1H), 4.75 (d, J=13.4 Hz, 1H), 4.66 (s, 1H), 4.25 (s, 1H), 4.00 (d, J=11.6 Hz, 1H), 3.92-3.69 (m, 3H), 3.17 (d, J=5.1 Hz, 1H), 2.19 (s, 3H), 2.12 (s, 3H) ppm.

MS m/z (ESI): 506.2 [M+1].

Example 3

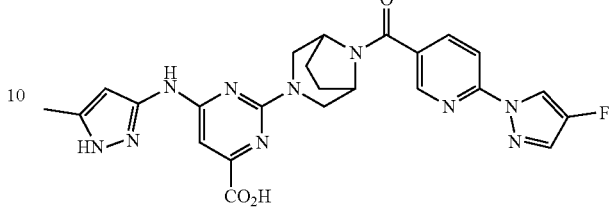

Synthesis of 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-formic Acid

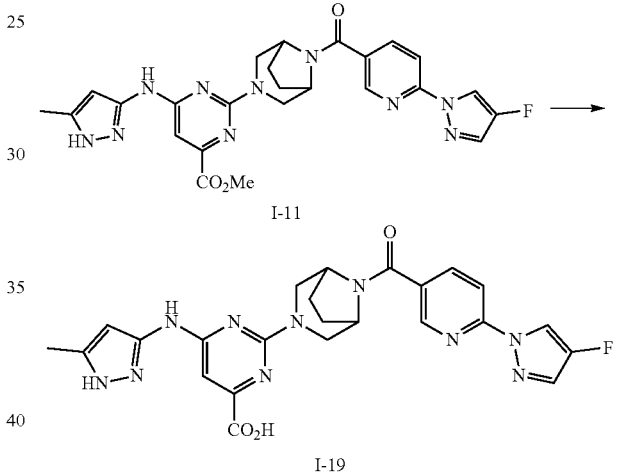

Methyl 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-carboxylate (I-11) (80 mg, 0.15 mmol) and lithium hydroxide monohydrate (42 mg, 1 mmol) were dissolved in 2.5 mL methanol/water (V:V=5:1) mixed solvent, and reacted overnight at room temperature. After methanol was removed under reduced pressure, 10 mL water was added to dilute, and 1 mol/L dilute hydrochloric acid was added to adjust the pH value to 2-3. Then ethyl acetate was added for extraction three times (20 mL×3). The organic phases were combined, washed with saturated brine once, dried, and filtered. After separation by silica gel column chromatography (the eluent and volume ratio: dichloromethane:methanol=10:1), 55 mg of 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-formic acid (I-19) was obtained, with a yield of 71%.

¹H NMR (400 MHz, DMSO-d₆) δ 12.12 (s, 1H), 10.02-9.62 (m, 1H), 8.77 (d, J=4.5 Hz, 1H), 8.65 (s, 1H), 8.18 (d, J=8.6 Hz, 1H), 8.00 (t, J=7.7 Hz, 2H), 6.85 (s, 1H), 6.23 (s, 1H), 4.92-4.03 (m, 4H), 3.48-3.00 (m, 2H), 2.21 (s, 3H), 1.91 (s, 2H), 1.68-1.65 (m, 2H) ppm.

MS m/z (ESI): 519.2 [M+1].

Example 4

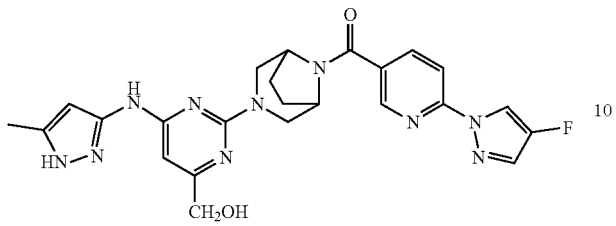

I-20

Synthesis of (6-(4-fluoro-1H-pyrazol-1-yl)pyridin-3-yl)(3-(4-(hydroxymethyl)-6-((5-methyl-1H-pyrazol-3-yl)amino)pyrimidin-2-yl)-3,8-diazabicyclo[3.2.1]octane-8-yl)methanone

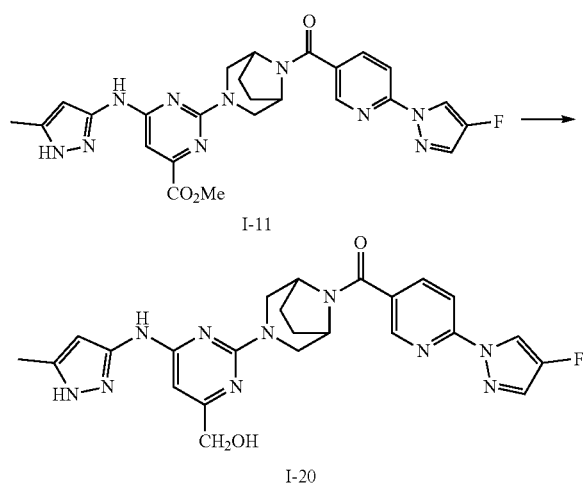

Methyl 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-carboxylate (I-11) (53 mg, 0.1 mmol) was dissolved in 1.5 mL of tetrahydrofuran and cooled to 0° C. before LiAlH₄ (11 mg, 0.3 mmol) was added. The reaction was slowly returned to room temperature. After the raw materials in the reaction monitored by TLC disappeared, the reaction was quenched by adding a small amount of sodium sulfate decahydrate and filtered. The filter cake was washed with ethyl acetate, and the organic phase was collected. After removing the solvent under reduced pressure and adding 30 mL of ethyl acetate, the organic phase was washed with water (5 mL×3) three times, followed by saturated brine once, dried over anhydrous sodium sulfate, filtered, and concentrated. After separation by silica gel column chromatography (the eluent and volume ratio: dichloromethane:methanol=20:1), 10 mg of (6-(4-fluoro-1H-pyrazol-1-yl)pyridin-3-yl)(3-(4-(hydroxymethyl)-6-((5-methyl-1H-pyrazol-3-yl)amino)pyrimidin-2-yl)-3,8-diazabicyclo[3.2.1]octane-8-yl)methanone (I-20) was obtained, with a yield of 20%.

$^1$H NMR (400 MHz, DMSO-$d_6$) δ 11.85 (s, 1H), 9.38 (s, 1H), 8.76 (d, J=4.4 Hz, 1H), 8.64 (d, J=2.2 Hz, 1H), 8.17 (dd, J=8.4, 2.2 Hz, 1H), 8.07-7.90 (m, 2H), 6.49 (s, 1H), 6.15 (s, 1H), 5.21 (t, J=5.9 Hz, 1H), 4.79 (s, 1H), 4.54-4.29 (m, 2H), 4.21 (d, J=6.0 Hz, 3H), 3.11 (d, J=12.8 Hz, 2H), 2.19 (s, 3H), 1.89 (s, 2H), 1.65 (s, 2H) ppm.

MS m/z (ESI): 505.2 [M+1]

Example 5

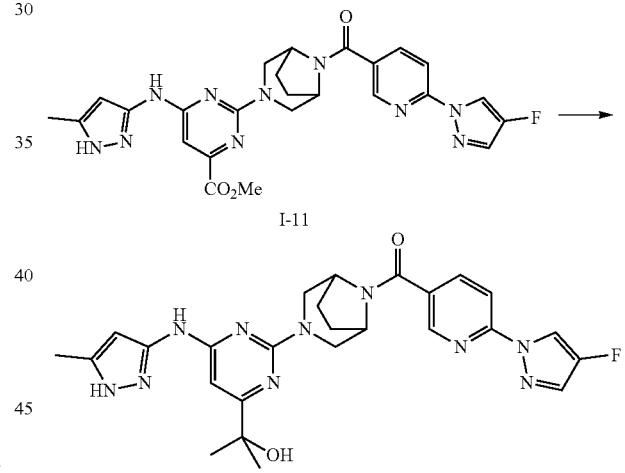

Synthesis of (6-(4-fluoro-1H-pyrazol-1-yl)pyridin-3-yl)(3-(4-(2-hydroxypropyl-2-yl)-6-((5-methyl-1H-pyrazol-3-yl)amino)pyrimidin-2-yl)-3,8-diazabicyclo[3.2.1]octane-8-yl)methanone Methyl 2-(8-(6-(4-fluoro-1H-pyrazol-1-yl)nicotinoyl)-3,8-diazabicyclo[3.2.1]octane-3-yl)-6-((5-methyl-1H-pyrazol-3-yl)amino)pyrimidin-4-carboxylate (I-11) (265 mg, 0.5 mmol) was dissolved in 5 mL of tetrahydrofuran and cooled to 0° C. under a nitrogen atmosphere, before a solution of 3 mol/L methylmagnesium iodide in ethyl ether was slowly added dropwise. After the addition, the reaction was returned to room temperature. After the reaction monitored by TLC completed, saturated ammonium chloride aqueous solution was added to quench the reaction. Then 100 mL of ethyl acetate was added. The organic phase was washed with water (20 mL×3) three times, followed by saturated brine once, dried, and filtered. After separation by silica gel column chromatography (the eluent and volume ratio: dichloromethane:methanol=30:1), 56 mg of (6-(4-fluoro-1H-pyrazol-1-yl)pyridin-3-yl)(3-(4-(2-hydroxypropyl-2-yl)-6-((5-methyl-1H-pyrazol-3-yl)amino)pyrimidin-2-yl)-3, 8-diazabicyclo[3.2.1]octane-8-yl)methanone (I-21) was obtained, with a yield of 22%.

$^1$H NMR (400 MHz, DMSO-d$_6$) δ 11.84 (s, 1H), 9.34 (s, 1H), 8.76 (d, J=4.5 Hz, 1H), 8.65 (s, 1H), 8.18 (d, J=8.7 Hz, 1H), 8.02 (d, J=4.2 Hz, 1H), 7.99 (d, J=8.7 Hz, 1H), 6.59 (s, 1H), 6.15 (s, 1H), 4.95 (s, 1H), 4.52-4.17 (m, 4H), 3.14-3.09 (m, 2H), 2.20 (s, 3H), 1.91 (s, 2H), 1.67 (s, 2H), 1.32 (s, 6H) ppm.

MS m/z (ESI): 533.3 [M+1]

Example 6

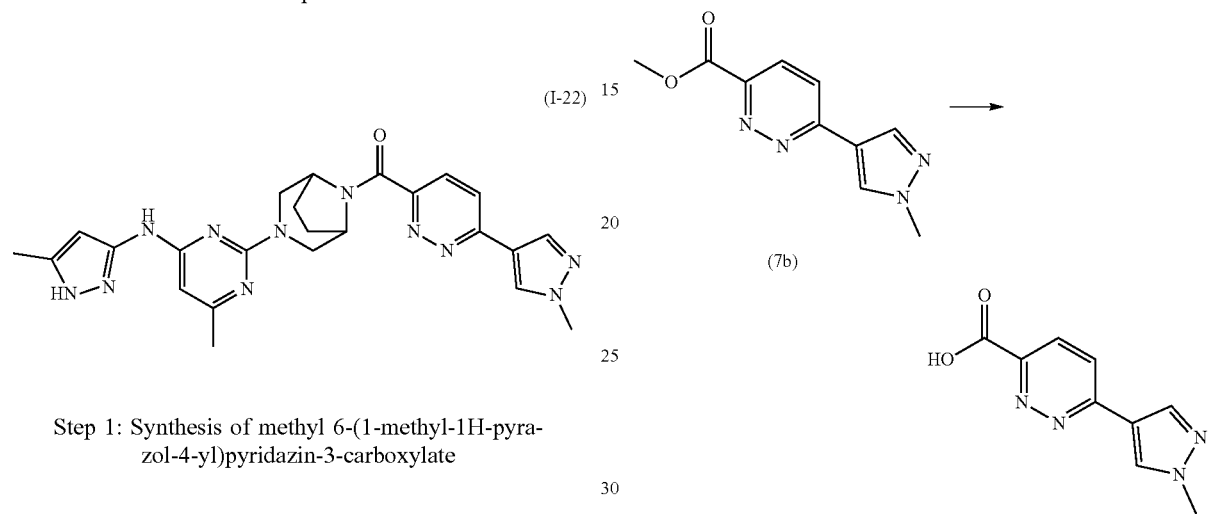

(I-22)

Step 1: Synthesis of methyl 6-(1-methyl-1H-pyrazol-4-yl)pyridazin-3-carboxylate

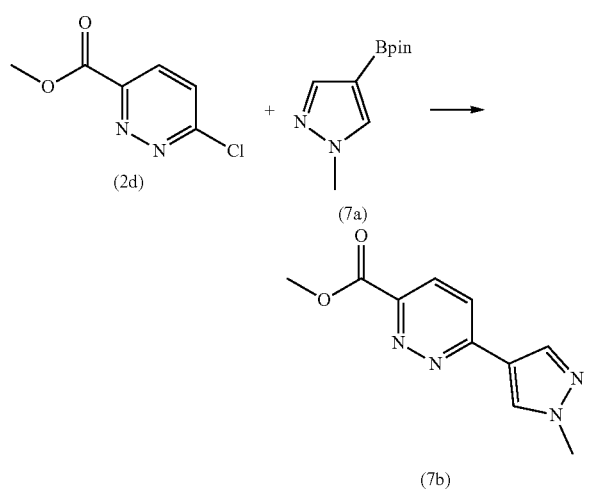

Methyl 6-chloro-pyridazin-3-carboxylate (2d) (1.73 g, 10 mmol), (1-methyl-1H-pyrazol-4-yl) boronic acid pinacol ester (7a) (4.16 g, 20 mmol), Pd$_2$(dba)$_3$ (410 mg, 0.5 mmol), PCy$_3$ (280 mg, 1 mmol) and potassium phosphate (6.4 g, 30 mmol) were dissolved in 35 mL of dioxane/water (V:V=6:1) mixed solvent, and reacted overnight at 100° C. under a nitrogen atmosphere. After the reaction, the temperature of the reaction solution was lowered to room temperature, the reaction solution was filtered through celite, and washed with ethyl acetate. After the organic solvent was removed under reduced pressure, 300 mL ethyl acetate was added. The organic phase was washed with water (40 mL×3) three times, followed by saturated brine once, and dried. After separation by silica gel column chromatography (the eluent and volume ratio: dichloromethane:methanol=30:1), 1.4 g of methyl 6-(1-methyl-1H-pyrazol-4-yl)pyridazin-3-carboxylate (7b) was obtained, with a yield of 65%.

MS m/z (ESI): 219.1 [M+1]

Step 2: Synthesis of 6-(1-methyl-1H-pyrazol-4-yl)pyridazin-3-formic Acid

Methyl 6-(1-methyl-1H-pyrazol-4-yl)pyridazin-3-carboxylate (7b) (1.4 g, 7 mmol) and lithium hydroxide monohydrate (580 mg, 14 mmol) were dissolved in 50 mL of methanol/water (V:V=2:1) mixed solvent, and reacted at 50° C. After the reaction monitored by LC-MS completed, methanol was removed under reduced pressure, 10 mL of water was added and 1 mol/L dilute hydrochloric acid was added to adjust the pH value to 2-3. A solid was precipitated, filtered and dried to obtain 580 mg of 6-(1-methyl-1H-pyrazol-4-yl)pyridazin-3-formic acid (7c), with a yield of 20%.

MS m/z (ESI): 205.2 [M+1]

Step 3: Synthesis of (6-(1-methyl-1H-pyrazol-4-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone

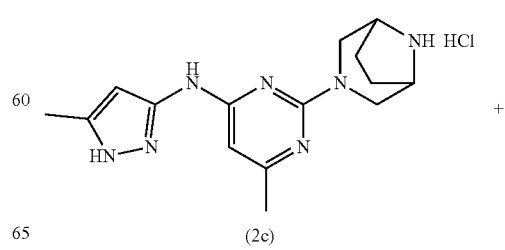

-continued

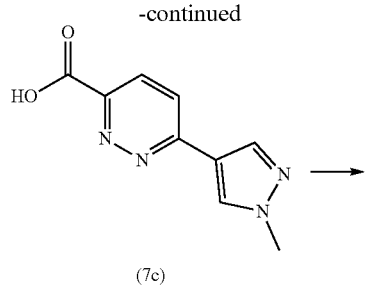

(7c)

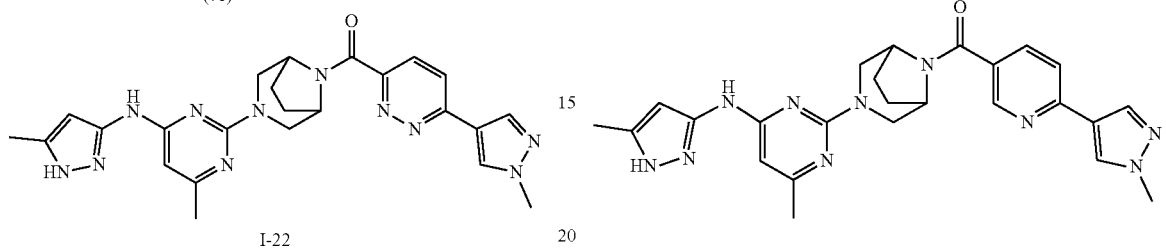

I-22

2-(3,8-diazabicyclo[3.2.1]octane-3-yl)-6-methyl-N-(5-methyl-1H-pyrazol-3-yl)pyrimidin-4-amine hydrochloride (2c) (201 mg, 0.6 mmol), 6-(1-methyl-1H-pyrazol-4-yl)pyridazin-3-formic acid (7c) (123 mg, 0.6 mmol) and PyBOP (468 mg, 0.9 mmol) were dissolved in 6 mL DMF and cooled to 0° C. before DIPEA (310 mg, 2.4 mmol) was added. The reaction was kept at 0° C. for 30 minutes, and 5 mL of water was added to quench the reaction. Then 100 mL of ethyl acetate was added. The organic phase was washed with water (15 mL×3) three times, followed by saturated brine once, dried over anhydrous sodium sulfate, and filtered, and the solvent was removed under reduced pressure. After separation by silica gel column chromatography (the eluent and volume ratio: dichloromethane:methanol=20:1), a crude product was obtained and further separated by silica gel preparation plate (the developing solvent and volume ratio: dichloromethane:methanol=10:1) to obtain 62 mg of (6-(1-methyl-1H-pyrazol-4-yl)pyridazin-3-yl)(3-(4-methyl-6-((5-methyl-1H-pyrazol-3-yl)amino)pyrimidin-2-yl)-3,8-diazabicyclo[3.2.1]octane-8-yl)methanone (I-22), with a yield of 22%.

$^1$H NMR (400 MHz, DMSO-d$_6$) δ 11.86 (s, 1H), 9.29 (s, 1H), 8.56 (s, 1H), 8.22 (s, 1H), 8.10 (d, J=8.8 Hz, 1H), 7.98 (d, J=8.8 Hz, 1H), 6.22 (s, 1H), 6.16 (s, 1H), 4.88 (d, J=5.8 Hz, 1H), 4.79 (s, 1H), 4.54 (d, J=12.7 Hz, 1H), 4.44 (d, J=12.6 Hz, 1H), 3.94 (s, 3H), 3.19 (d, J=12.7 Hz, 1H), 3.11 (d, J=12.8 Hz, 1H), 2.20 (s, 3H), 2.12 (s, 3H), 1.92 (d, J=8.4 Hz, 2H), 1.71 (d, J=8.2 Hz, 2H) ppm.

MS m/z (ESI): 486.3 [M+1].

With reference to Example 6, the following compounds can be prepared:

Compound (I-23)

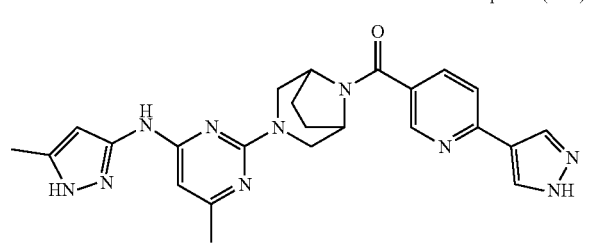

$^1$H NMR (400 MHz, DMSO-d$_6$) δ 13.16 (s, 1H), 11.84 (s, 1H), 9.27 (s, 1H), 8.67 (s, 1H), 8.42 (s, 1H), 8.13 (s, 1H), 7.92 (d, J=8.2 Hz, 1H), 7.78 (d, J=8.2 Hz, 1H), 6.22 (s, 1H), 6.13 (s, 1H), 5.08-4.13 (m, 4H), 3.10 (d, J=12.8 Hz, 2H), 2.19 (s, 3H), 2.12 (s, 3H), 1.88 (s, 2H), 1.65 (d, J=9.7 Hz, 2H) ppm.

MS m/z (ESI): 471.2 [M+1].

Compound (I-24)

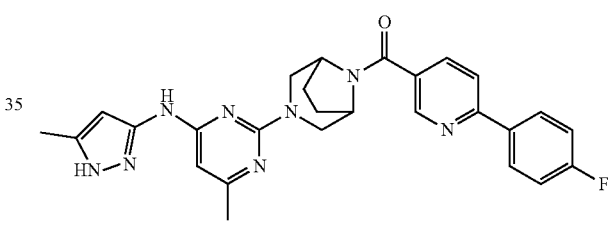

$^1$H NMR (400 MHz, DMSO-d$_6$) δ 11.84 (s, 1H), 9.28 (s, 1H), 8.67 (s, 1H), 8.37 (s, 1H), 8.07 (s, 1H), 7.92 (dd, J=8.1, 2.2 Hz, 1H), 7.73 (d, J=8.1 Hz, 1H), 6.21 (s, 1H), 6.13 (s, 1H), 4.78 (s, 1H), 4.55-4.32 (m, 2H), 4.21 (s, 1H), 3.90 (s, 3H), 3.10 (d, J=12.7 Hz, 2H), 2.19 (s, 3H), 2.12 (s, 3H), 1.88 (s, 2H), 1.65 (d, J=9.8 Hz, 2H) ppm.

MS m/z (ESI): 485.3 [M+1].

Compound (I-25)

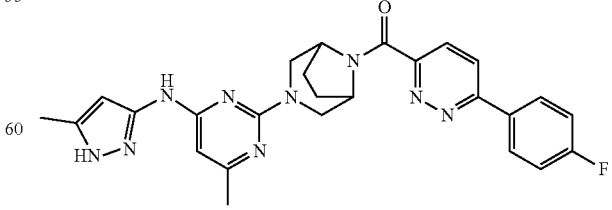

$^1$H NMR (400 MHz, DMSO-d$_6$) δ 11.84 (s, 1H), 9.27 (s, 1H), 8.82 (s, 1H), 8.21 (dd, J=8.5, 5.5 Hz, 2H), 8.06 (t, J=6.5 Hz, 2H), 7.35 (t, J=8.7 Hz, 2H), 6.22 (s, 1H), 6.13 (s, 1H), 4.86-4.75 (m, 1H), 4.55-4.35 (m, 2H), 4.24-4.16 (m, 1H), 3.13-3.10 (m, 2H), 2.19 (s, 3H), 2.12 (s, 3H), 1.93-1.86 (m, 2H), 1.67-1.65 (m, 2H) ppm.

MS m/z (ESI): 499.2 [M+1].

Compound (I-26)

$^1$H NMR (400 MHz, DMSO-d$_6$) δ 11.86 (s, 1H), 9.29 (s, 1H), 8.41 (d, J=8.9 Hz, 1H), 8.31 (d, J=8.6 Hz, 2H), 8.09 (d, J=8.8 Hz, 1H), 7.43 (t, J=8.7 Hz, 2H), 6.23 (s, 1H), 6.15 (s,

1H), 4.93-4.87 (m, 1H), 4.74 (s, 1H), 4.56 (d, J=12.7 Hz, 1H), 4.45 (d, J=12.6 Hz, 1H), 3.15-3.12 (m, 2H), 2.20 (s, 3H), 2.12 (s, 3H), 1.94 (d, J=10.9 Hz, 2H), 1.72 (d, J=8.7 Hz, 2H) ppm.

MS m/z (ESI): 500.2 [M+1].

Compound (I-27)

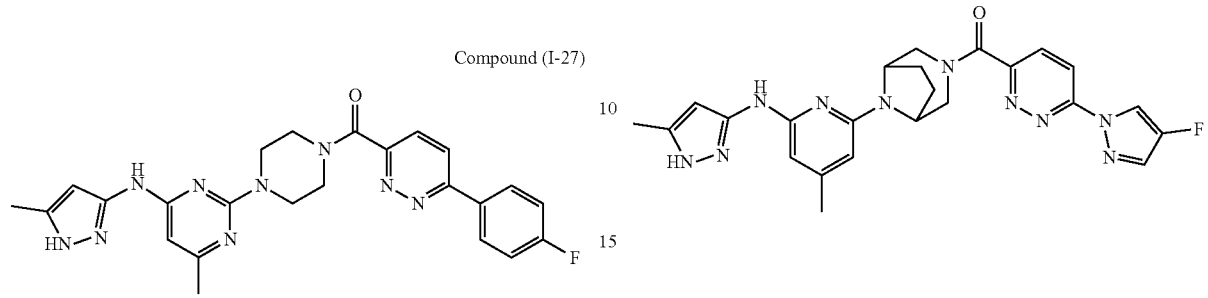

$^1$H NMR (400 MHz, DMSO-d$_6$) δ 9.46-9.10 (m, 1H), 8.41 (d, J=8.7 Hz, 1H), 8.30 (dd, J=8.4, 5.5 Hz, 2H), 8.15 (s, 1H), 8.00 (d, J=8.7 Hz, 1H), 7.44 (t, J=8.6 Hz, 2H), 6.23 (s, 1H), 6.12 (s, 1H), 3.92-3.84 (m, 2H), 3.84-3.67 (m, 4H), 3.59-3.57 (m, 2H), 2.18 (s, 3H), 2.13 (s, 3H) ppm.

MS m/z (ESI): 474.2 [M+1].

Compound (I-28)

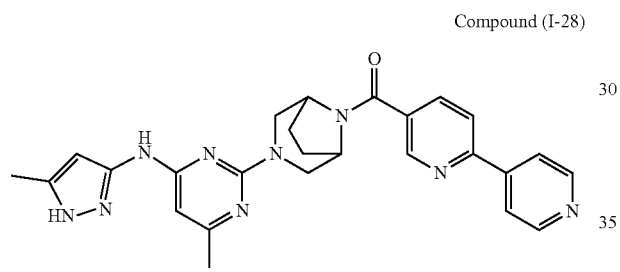 [SMILES: Cc1cc(Nc2cc(C)[nH]n2)nc(N2CC3CCC(C2)N3C(=O)c2ccc(-c3ccc(F)cc3)nc2)n1]

$^1$H NMR (400 MHz, DMSO-d$_6$) δ 11.85 (s, 1H), 9.30 (s, 1H), 8.89 (s, 1H), 8.74 (s, 2H), 8.23 (d, J=8.1 Hz, 1H), 8.13 (d, J=11.7 Hz, 3H), 6.21 (s, 1H), 6.13 (s, 1H), 4.82 (s, 1H), 4.44 (d, J=44.1 Hz, 2H), 4.18-4.11 (m, 1H), 3.20-3.03 (m, 2H), 2.19 (s, 3H), 2.12 (s, 3H), 1.91 (s, 2H), 1.66 (s, 2H) ppm.

MS m/z (ESI): 482.2 [M+1].

Compound (I-29)

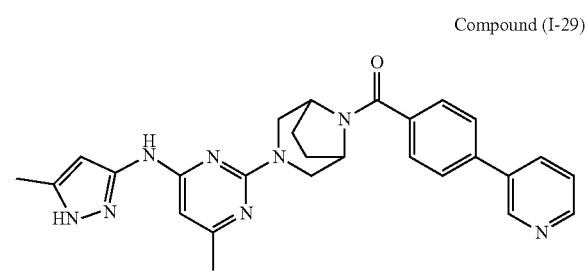 [SMILES: Cc1cc(Nc2cc(C)[nH]n2)nc(N2CC3CCC(C2)N3C(=O)c2ccc(-c3cccnc3)cc2)n1]

$^1$H NMR (400 MHz, DMSO-d$_6$) δ 11.84 (s, 1H), 9.28 (s, 1H), 8.95 (s, 1H), 8.61 (d, J=4.6 Hz, 1H), 8.14 (d, J=8.0 Hz, 1H), 7.84 (d, J=7.8 Hz, 2H), 7.67 (d, J=7.8 Hz, 2H), 7.52 (dd, J=7.9, 4.8 Hz, 1H), 6.23 (s, 1H), 6.13 (s, 1H), 4.80 (s, 1H), 4.47 (s, 1H), 4.38 (s, 1H), 4.18 (s, 1H), 3.12-3.08 (m, 2H), 2.19 (s, 3H), 2.12 (s, 3H), 1.87 (s, 2H), 1.66 (s, 2H) ppm.

MS m/z (ESI): 481.3 [M+1].

Example 7

I-30

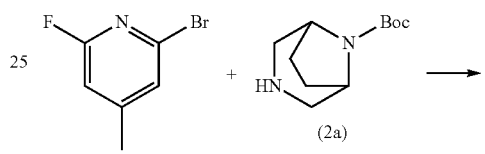

Step 1: Synthesis of methyl 3-(6-bromo-4-methylpyridin-2-yl)-3,8-diazabicyclo[3.2.1]octane-8-carboxylate

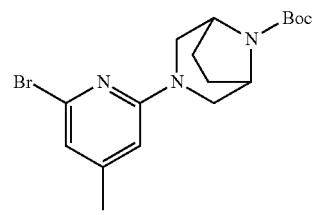

2-fluoro-4-methyl-6-bromo-pyridine (8a) (1.9 g, 10 mmol), tert-butyl 3,8-diazabicyclo[3.2.1]octane-8-carboxylate (2a) (2.54 g, 12 mmol), and K$_2$CO$_3$ (4.14 g, 30 mmol) were dissolved in 25 mL DMF, and reacted at 110° C. with stirring. After the raw materials in the reaction monitored by TLC disappeared, the reaction was returned to room temperature, and 10 mL of water was added to quench the reaction. Then 150 mL of ethyl acetate was added. The organic phase was washed with water three times (25 mL×3), followed by saturated brine once, dried over anhydrous sodium sulfate, and filtered, and the solvent was removed under reduced pressure. After the product was separated by silica gel column chromatography (the developing solvent and volume ratio: petroleum ether:ethyl acetate=7:1) and dried under vacuum, 820 mg of methyl 3-(6-bromo-4-methylpyridin-2-yl)-3,8-diazabicyclo[3.2.1]octane-8-carboxylate (8b) was obtained, with a yield of 22%.

MS m/z (ESI): 382.1 [M+1]

Step 2: Synthesis of methyl 3-(4-methyl-6-((5-methyl-1H-pyrazol-3-yl)amino)pyridin-2-yl)-3,8-diazabicyclo[3.2.1]octane-8-carboxylate

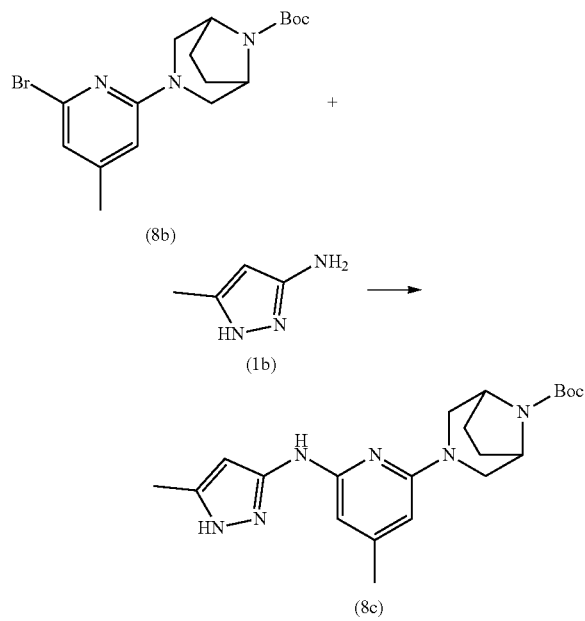

Under a nitrogen atmosphere, methyl 3-(6-bromo-4-methylpyridin-2-yl)-3,8-diazabicyclo[3.2.1]octane-8-carboxylate (8b) (754 mg, 1.97 mmol), 5-methyl-1H-3-aminopyrazole (1b) (380 mg, 3.94 mmol), $Pd_2(dba)_3$ (357 mg, 0.39 mmol), t-BuXphos (336 mg, 0.79 mmol) and potassium acetate (579 mg, 5.91 mmol) were dissolved in 17 mL DMAc, and reacted at 140° C. with stirring. After the reaction monitored by TLC completed, the reaction was returned to room temperature. Then 100 mL of ethyl acetate was added. The organic phase was washed with water three times (20 mL×3), followed by saturated brine once, dried over anhydrous sodium sulfate, filtered, and concentrated. After the product was separated by silica gel column chromatography (the eluent and volume ratio: petroleum ether: ethyl acetate=1:1), 520 mg of methyl 3-(4-methyl-6-((5-methyl-1H-pyrazol-3-yl)amino)pyridin-2-yl)-3,8-diazabicyclo[3.2.1]octane-8-carboxylate (8c) was obtained, with a yield of 61%.

MS m/z (ESI): 399.3 [M+1]

Step 3: Synthesis of 6-(3,8-diazabicyclo[3.2.1]octane-3-yl)-4-methyl-N-(5-methyl-1H-pyrazol-3-yl)pyridin-2-amine Hydrochloride

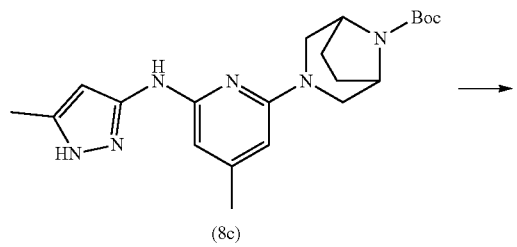

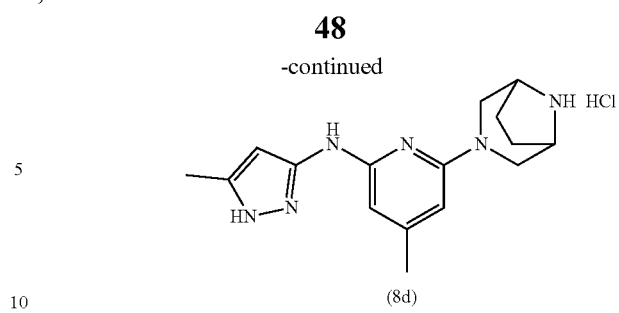

Methyl 3-(4-methyl-6-((5-methyl-1H-pyrazol-3-yl)amino)pyridin-2-yl)-3,8-diazabicyclo[3.2.1]octane-8-carboxylate (8c) (520 mg, 1.3 mmol) was dissolved in 8 mL of 1,4-dioxane, 10 mL of a solution of hydrogen chloride in 1,4-dioxane with a concentration of 2.6 mol/L was added dropwise, and reacted at 50° C. After the raw material in the reaction monitored by LC-MS disappeared, the reaction was returned to room temperature. The solvent was removed under reduced pressure and 20 mL of ethyl acetate was added. The mixture was stirred for 10 minutes, filtered, and the filter cake was washed with ethyl acetate followed by ethyl ether, and dried under vacuum to obtain 324 mg of 6-(3,8-diazabicyclo[3.2.1]octane-3-yl)-4-methyl-N-(5-methyl-1H-pyrazol-3-yl)pyridin-2-amine hydrochloride (8d), with a yield of 74%.

MS m/z (ESI): 299.2 [M+1]

Step 4: Synthesis of (6-(4-fluoro-1H-pyrazol-1-yl)pyridazin-3-yl)(8-(4-methyl-6-((5-methyl-1H-pyrazol-3-yl)amino)pyridin-2-yl)-3,8-diazabicyclo[3.2.1]octane-3-yl)methanone

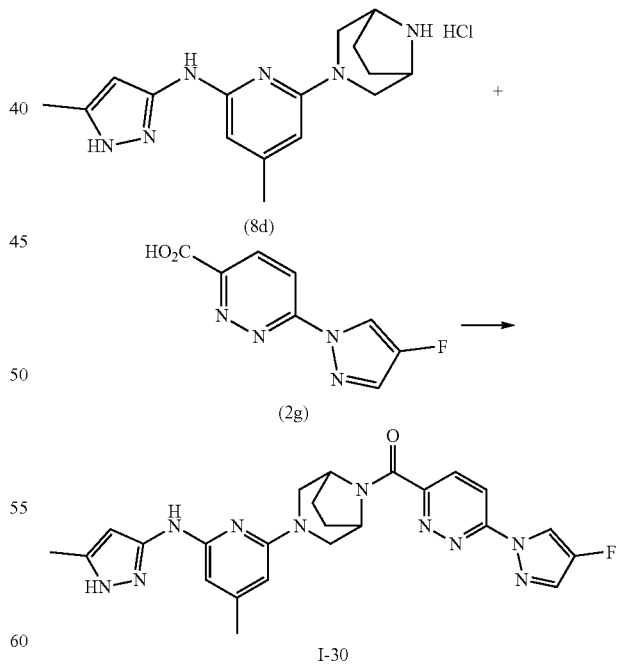

6-(3,8-diazabicyclo[3.2.1]octane-3-yl)-4-methyl-N-(5-methyl-1H-pyrazol-3-yl)pyridin-2-amine hydrochloride (8d) (184 mg, 0.55 mmol), 6-(4-fluoro-1H-pyrazol-1-yl)pyridazin-3-formic acid (2g) (104 mg, 0.5 mmol) and PyBOP (289 mg, 0.75 mmol) were dissolved in 5 mL DMF, and the reaction solution was cooled to 0° C. before DIPEA (204 mg, 2 mmol) was added. The reaction was kept at 0° C. for 20 minutes, and 3 mL of water was added to quench the reaction. Then 50 mL of ethyl acetate was added. The organic phase was washed with water (10 mL×3) three times, followed by saturated brine once, dried over anhydrous sodium sulfate, filtered, and concentrated. After separation by silica gel column chromatography (the eluent and volume ratio: dichloromethane:methanol=15:1), 63 mg of (6-(4-fluoro-1H-pyrazol-1-yl)pyridazin-3-yl)(8-(4-methyl-6-((5-methyl-1H-pyrazol-3-yl)amino)pyridin-2-yl)-3,8-diazabicyclo[3.2.1]octan-3-yl)methanone (I-30) was obtained, with a yield of 26%.

$^1$H NMR (400 MHz, DMSO) δ 9.07 (d, J=4.2 Hz, 1H), 8.61 (s, 1H), 8.34 (d, J=9.1 Hz, 1H), 8.21 (d, J=9.1 Hz, 1H), 8.15 (d, J=3.4 Hz, 2H), 6.34 (s, 1H), 5.99 (s, 1H), 5.90 (s, 1H), 4.91 (s, 1H), 4.78 (s, 1H), 4.11 (d, J=12.1 Hz, 1H), 3.98 (d, J=11.4 Hz, 1H), 3.16 (d, J=8.3 Hz, 1H), 3.04 (d, J=11.7 Hz, 1H), 2.18 (s, 3H), 2.12 (s, 3H), 1.95 (d, J=8.9 Hz, 2H), 1.80 (d, J=8.4 Hz, 2H) ppm.

MS m/z (ESI): 489.3 [M+1]

Biological Evaluation

Test Example 1. Determination of the Activity of the Compound of the Present Disclosure on RET Kinase In this method, HTRF®KinEASE-TK Tyrosine Kinase Kit (Cat. No. 62TK0PEB) of Cisbio was used to determine the degree of phosphorylation of biotinylated polypeptide substrates by time-resolved fluorescence energy transfer (TR-FRET). Human RET protein (RET kinase) was purchased from Carna bioscience (Japan, Cat. No. 08-159-5 μg).

The experimental steps are as follows:
(1) The test compound (the compound of the present disclosure, and compound 164 in WO2018017983A1 as a control) was dissolved in 100% DMSO to a final concentration of 10 mM.
(2) 4 μL of the test compound solution prepared in step (1) was dissolved with 46 μL of 100% DMSO, and the solution obtained in this step was numbered as No. 2.
(3) No. 2 solution was subjected to subsequent gradient dilution with a dilution factor of 5 times (i.e. 20 μL of 100% DMSO was added to 5 μL of the compound), a total of 9 gradients, numbered 3 to 11.
Note: No. 2 was not used for the dilution in step (4).
(Unless otherwise specified, the following steps need to be carried out on ice)
(4) The buffer provided in the kit (Cisbio, Cat. No. 62TK0PEB) was used to continuously serially dilute the solutions numbered from 3 to 11 with a dilution factor of 20 times (that is, adding 19 μL of buffer to the solutions numbered from 3 to 11). At this time, the final concentration range of the test compound in the system No. 3 to 11 was 3200 nM~0.008 nM (9 gradients), and the final concentration of DMSO was 2%.
(5) 9 compound solutions of gradient concentration in step (4) were added into a 384-well plate in order according to their concentration at 4 μL per well, and two duplicate wells were set.
(6) 2 μL of human RET protein was added to each well and incubated on ice for 10 minutes.
(7) 2 μL of ATP (Sigma #A7699) and 2 μL of biotinylated polypeptide substrate (Cisbio, Cat. No. 62TK0PEB) were added to each well to start the phosphorylation reaction, and incubated at 37° C. for half an hour.
(8) 5 μL of anti-phosphotyrosine antibody coupled with europium compound (provided in the kit, Cat. No. 62TK0PEB) and 5 μL of streptavidin coupled with modified allophycocyanin XL665 (Cisbio, Cat. No. 62TK0PEB) were added to each well.
(9) The plate was continued to incubate for 1 hour at room temperature. After the incubation, the TF-FRET mode of the microplate reader (BMG Labtech, model: FLUOStar Omega) was adopted to measure the fluorescence intensity at an excitation wavelength of 304 nM and emission wavelengths of 615 nM and 665 nM in each well. The ratio would be calculated automatically.
(10) By comparing the fluorescence intensity ratio in the control group, the inhibition rate of the compound at each concentration was calculated, and GraphPad Prism 5 was used to perform curve fitting with logarithmic concentration-inhibition rate to calculate the $IC_{50}$ value of the compound. The results are shown in Table 2 below.

The selected control kinase is another receptor tyrosine kinase, KDR, with similar structure to RET kinase, purchased from Carna bioscience (Japan, Cat. No. 08-191-5 μg). The step of gradient dilution was the same as that of RET kinase, and the final concentration range of the test compound in the reaction system was 16000 nM~0.04 nM (No. 2-10 solutions were used for the gradient dilution in step 4). Other reaction conditions were the same as above, and the final concentration of DMSO was 2%. The calculation method for the $IC_{50}$ value of KDR kinase inhibition by the test compound was the same as the calculation method for the $IC_{50}$ value of RET kinase inhibition.

TABLE 2

$IC_{50}$ values of the compounds of the present disclosure and compound 164 for inhibition of RET kinase and KDR kinase

| Compound No. | RET ($IC_{50}$/nM) | KDR ($IC_{50}$/nM) |
| --- | --- | --- |
| I-1 | 12.5 | 1132 |
| I-2 | 11.8 | 851 |
| I-4 | 1.4 | 80 |
| I-5 | 6.2 | 149 |
| I-7 | 10.3 | 391 |
| I-8 | 1.7 | 107 |
| I-9 | 8.6 | 304 |
| I-10 | 7.3 | 1550 |
| I-11 | 24.7 | 1020 |
| I-12 | 0.6 | 180 |
| I-13 | 1.5 | 78 |
| I-14 | 3.9 | 141 |
| I-16 | 8.0 | 738 |
| I-19 | 25.6 | 2760 |
| I-20 | 3.0 | 1550 |
| I-22 | 2.0 | 221 |
| I-24 | 8.1 | 374 |
| I-25 | 5.6 | 260 |
| I-28 | 2.6 | 467 |
| I-30 | 1.8 | 95 |
| 164 | 73 | 2300 |

It can be seen from the above table that the compounds of the present disclosure had a significant inhibitory effect on RET kinase activity, and the inhibitory effect was significantly better than that of the compound 164 in WO2018017983A1. The inhibitory activity of the compounds of the present disclosure on RET kinase was also significantly better than the inhibitory activity on KDR kinase. Therefore, the compound of the present disclosure can be used as a kind of effective selective RET kinase inhibitors.

The structural formula of compound 164 is shown below, and its structure and preparation method are disclosed in WO2018017983A1.

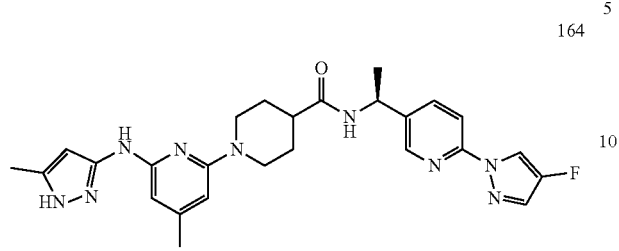

164

What is claimed is:

1. A compound represented by formula (I), or a stereoisomer or tautomer thereof, or a pharmaceutically acceptable salt thereof:

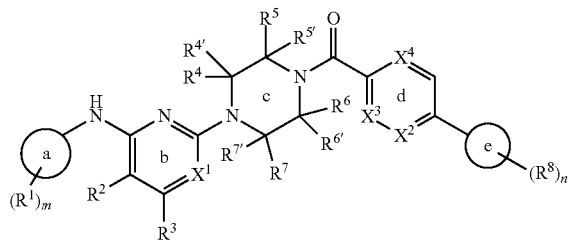

(I)

wherein
ring a is selected from pyrazolyl, pyridyl and pyridonyl;
$R^1$ is selected from hydrogen, $C_1$-$C_3$ alkyl, and $C_3$-$C_6$ cycloalkyl, wherein the $C_1$-$C_3$ alkyl and $C_3$-$C_6$ cycloalkyl are optionally further substituted with one or more halogen atoms;
$X^1$ is selected from CH and N;
$R^2$ is selected from hydrogen and $C_1$-$C_6$ alkyl;
$R^3$ is selected from hydrogen, cyano, $C_1$-$C_6$ alkyl, $C_1$-$C_5$ primary alcohol group, $C_3$-$C_7$ tertiary alcohol group, $C_1$-$C_3$ alkoxy, $C_3$-$C_6$ cycloalkyl, and —$R^9CO_2R^{10}$, wherein the $C_1$-$C_6$ alkyl, $C_1$-$C_5$ primary alcohol group, $C_3$-$C_7$ tertiary alcohol group, $C_1$-$C_3$ alkoxy, and $C_3$-$C_6$ cycloalkyl are optionally further substituted with one or more halogen atoms;
alternatively, $R^2$, $R^3$ and the two carbon atoms attached thereto together form an aryl group, and the aryl group is optionally further substituted with one or more halogen atoms or $C_1$-$C_6$ alkyl;
$R^9$ is selected from a chemical bond and $C_1$-$C_4$ alkylene group;
$R^{10}$ is selected from hydrogen and $C_1$-$C_6$ alkyl;
$X^2$, $X^3$, and $X^4$ are selected from CH and N; when $X^2$ is N, at most one of $X^3$ and $X^4$ is N; when $X^2$ is CH, $X^3$ and $X^4$ are both CH;
$R^4$, $R^{4'}$, $R^5$, $R^{5'}$, $R^6$, $R^{6'}$, $R^7$, and $R^{7'}$ are independently selected from hydrogen, $C_1$-$C_3$ alkyl and $C_1$-$C_4$ alkoxy, wherein the $C_1$-$C_3$ alkyl is optionally further substituted with one or more hydroxy, carboxy or cyano groups;
alternatively, $R^4$ and $R^{4'}$, $R^5$ and $R^{5'}$, $R^6$ and $R^{6'}$, or $R^7$ and $R^{7'}$ are attached together to form —$(CH_2)_2$—, —$(CH_2)_3$—, —$CH(CH_3)CH_2$—, —$OCH_2CH_2$—, or —$CH_2OCH_2$—;
alternatively, $R^4$ and $R^5$, $R^4$ and $R^6$, $R^4$ and $R^7$, $R^{4'}$ and $R^{5'}$, $R^{4'}$ and $R^{6'}$, $R^{4'}$ and $R^{7'}$, $R^5$ and $R^6$, $R^5$ and $R^7$, $R^{5'}$ and $R^{6'}$, $R^{5'}$ and $R^{7'}$, $R^6$ and $R^7$ or $R^{6'}$ and $R^{7'}$ are attached together to form —$(CH_2)_q$— or —$(CH_2OCH_2)$—;
alternatively, $R^4$ and $R^{4'}$, $R^5$ and $R^{5'}$, $R^6$ and $R^{6'}$, or $R^7$ and $R^{7'}$ together represent =O;
ring e is selected from pyrazolyl, pyridyl, phenyl and 3-azabicyclo[3.1.0]hexane-3-yl;
$R^8$ is independently selected from hydrogen, halogen, cyano, $C_1$-$C_3$ alkyl, $C_1$-$C_3$ alkoxy, and $C_3$-$C_6$ cycloalkyl, wherein the $C_1$-$C_3$ alkyl, $C_1$-$C_3$ alkoxy, and $C_3$-$C_6$ cycloalkyl are optionally further substituted with one or more halogen atoms;
m is 1 or 2;
n is 1, 2 or 3; and
q is 2 or 3.

2. The compound, or a stereoisomer or tautomer thereof, or a pharmaceutically acceptable salt thereof according to claim 1, which is a compound represented by formula (II), or a stereoisomer or tautomer thereof, or a pharmaceutically acceptable salt thereof:

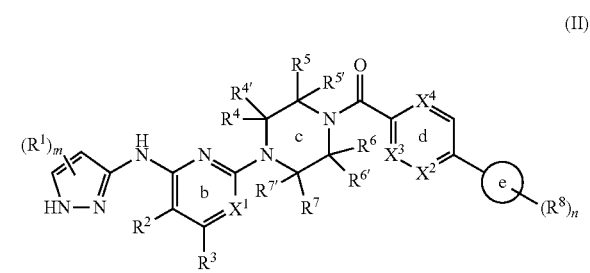

(II)

wherein:
ring e, $X^1$, $X^2$, $X^3$, $X^4$, $R^1$, $R^2$, $R^3$, $R^4$, $R^{4'}$, $R^5$, $R^{5'}$, $R^6$, $R^{6'}$, $R^7$, $R^{7'}$, $R^8$, m, and n have the same definitions as in claim 1.

3. The compound, or a stereoisomer or tautomer thereof, or a pharmaceutically acceptable salt thereof according to claim 1, wherein $R^3$ is selected from hydrogen, cyano, $C_1$-$C_6$ alkyl, —$CH_2OH$, —$C(CH_3)_2OH$, $C_1$-$C_3$ alkoxy, $C_3$-$C_6$ cycloalkyl, and —$R^9CO_2R^{10}$, wherein the $C_1$-$C_6$ alkyl is optionally further substituted with one or more halogen atoms; alternatively, $R^2$, $R^3$ and the two carbon atoms attached thereto together form an aryl group, which is optionally further substituted with one or more halogen atoms or $C_1$-$C_6$ alkyl;
$R^9$ is selected from a chemical bond and $C_1$-$C_4$ alkylene group;
$R^{10}$ is selected from hydrogen and $C_1$-$C_6$ alkyl.

4. The compound, or a stereoisomer or tautomer thereof, or a pharmaceutically acceptable salt thereof according to claim 3, wherein $R^3$ is selected from hydrogen, methyl, trifluoromethyl, —$CH_2OH$, —$C(CH_3)_2OH$, —COOH and —COOMe; alternatively, $R^2$, $R^3$ and the two carbon atoms attached thereto together form a benzene ring.

5. The compound, or a stereoisomer or tautomer thereof, or a pharmaceutically acceptable salt thereof according to claim 1, wherein $R^4$, $R^{4'}$, $R^5$, $R^{5'}$, $R^6$, $R^{6'}$, $R^7$, and $R^{7'}$ are each independently selected from hydrogen, methyl, —$CH_2OH$ and —$CH_2CH_2OH$; alternatively, $R^4$ and $R^{4'}$, $R^5$ and $R^{5'}$, $R^6$ and $R^{6'}$, or $R^7$ and $R^{7'}$ are attached together to form —$(CH_2)_2$—, —$OCH_2CH_2$— or —$CH_2OCH_2$—; alternatively, $R^4$ and $R^5$, $R^4$ and $R^6$, $R^4$ and $R^7$, $R^{4'}$ and $R^{5'}$, $R^{4'}$ and $R^{6'}$, $R^{4'}$ and $R^{7'}$, $R^5$ and $R^6$, $R^5$ and $R^7$, $R^{5'}$ and $R^{6'}$, $R^{5'}$ and R[7'], R[6] and R[7] or R[6'] and R[7'] are attached together to form —CH$_2$OCH$_2$— or —(CH$_2$)$_2$—.

6. The compound, or a stereoisomer or tautomer thereof, or a pharmaceutically acceptable salt thereof according to claim 1, wherein R[8] is independently selected from hydrogen, halogen, cyano, and C$_1$-C$_3$ alkyl.

7. The compound, or a stereoisomer or tautomer thereof, or a pharmaceutically acceptable salt thereof according to claim 1, wherein the compound is selected from the following compounds:

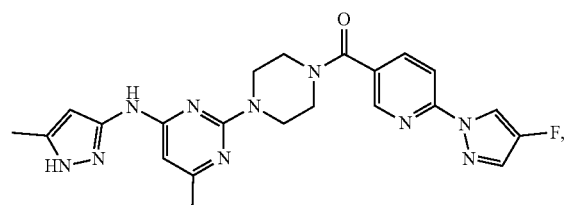

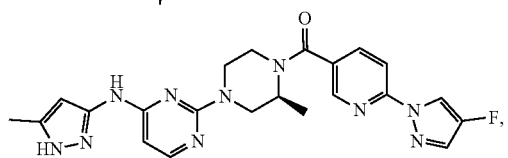

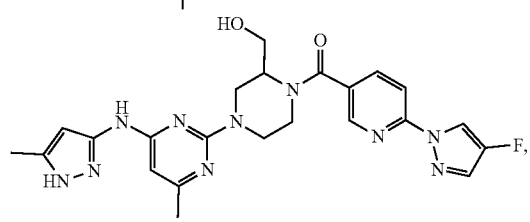

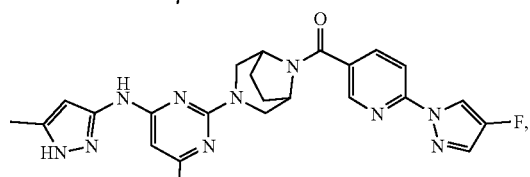

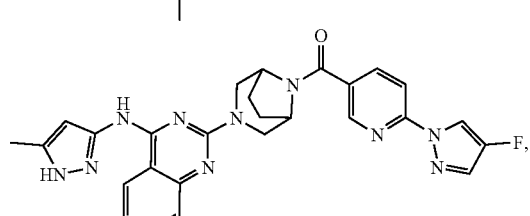

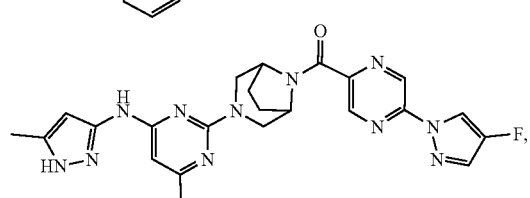

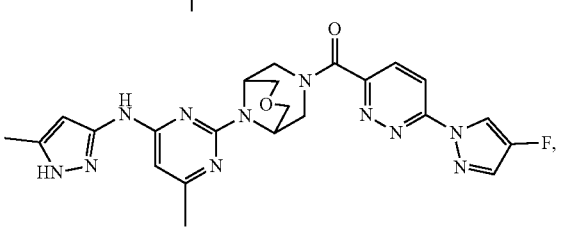

-continued

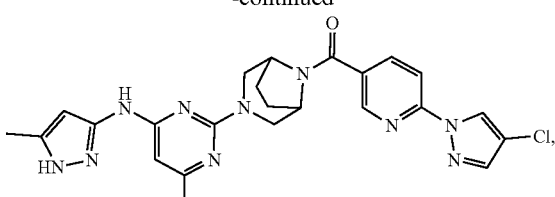

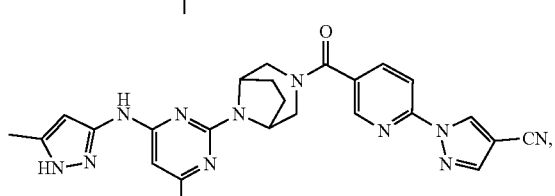

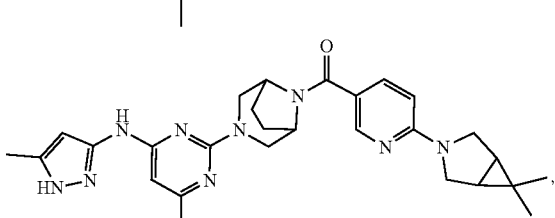

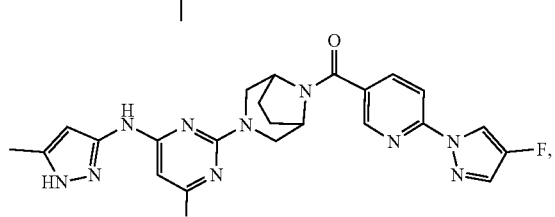

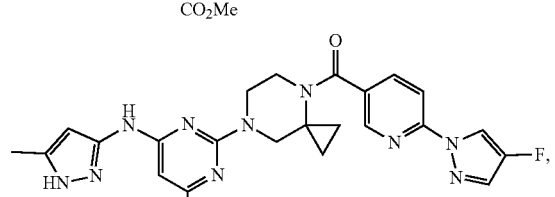

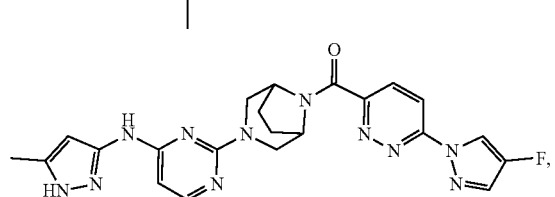

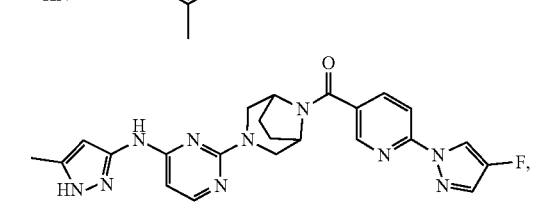

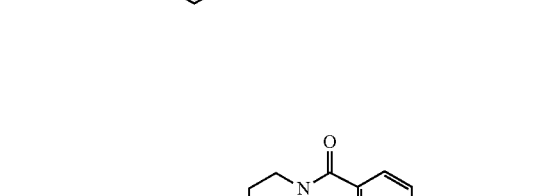

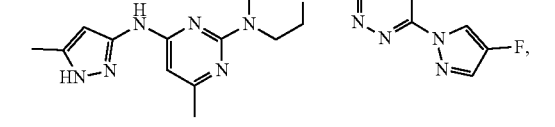

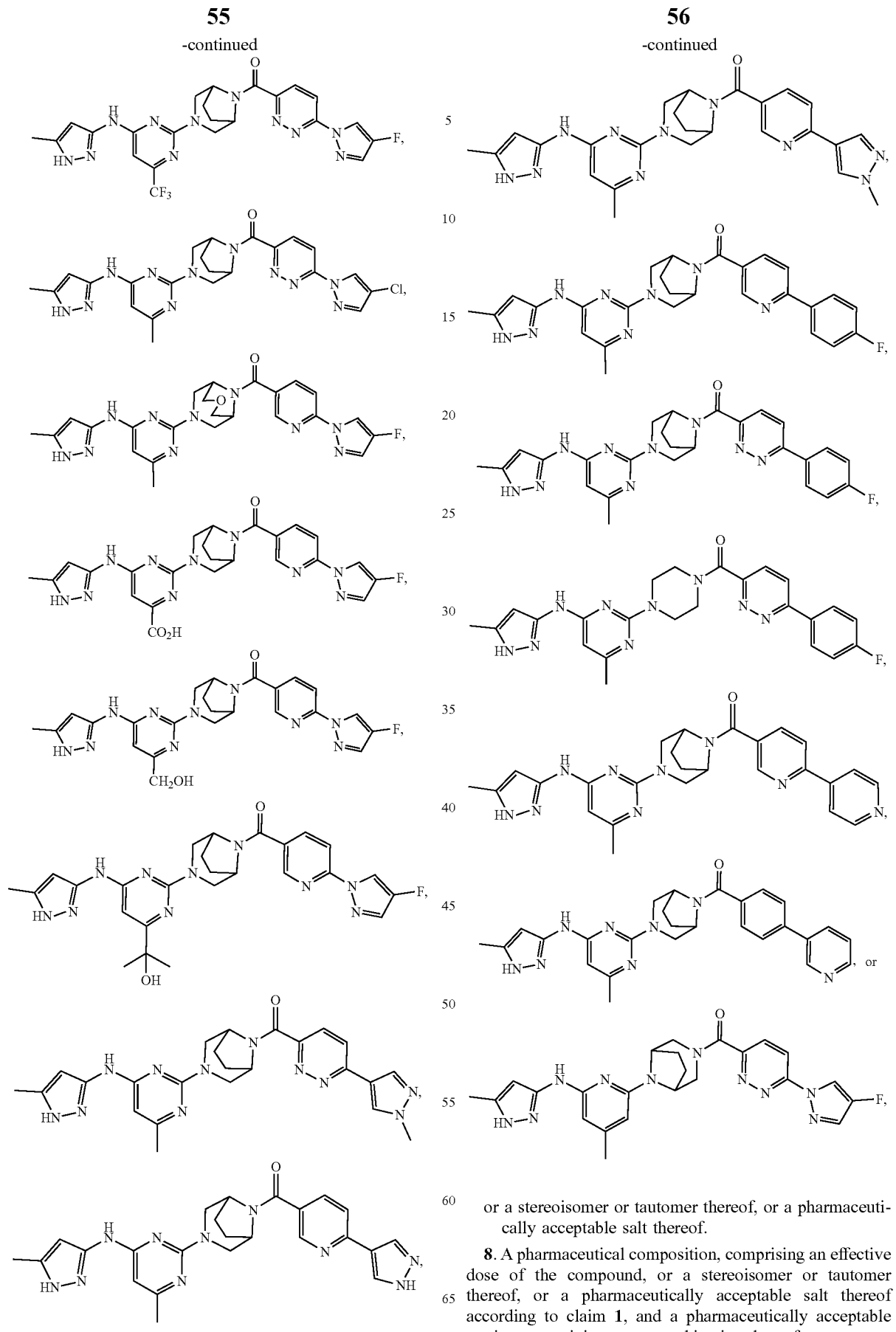
or a stereoisomer or tautomer thereof, or a pharmaceutically acceptable salt thereof.
8. A pharmaceutical composition, comprising an effective dose of the compound, or a stereoisomer or tautomer thereof, or a pharmaceutically acceptable salt thereof according to claim 1, and a pharmaceutically acceptable carrier, an excipient, or a combination thereof.

9. A method of manufacturing a rearranged during transfection kinase inhibitor, comprising using the compound, or a stereoisomer or tautomer thereof, or a pharmaceutically acceptable salt thereof according to claim 1 as active pharmaceutical ingredient.

10. A method of treating a disease driven by the rearranged during transfection gene, comprising administering the compound, or a stereoisomer or tautomer thereof, or a pharmaceutically acceptable salt thereof according to claim 1 to a subject in need thereof.

11. The compound, or a stereoisomer or tautomer thereof, or a pharmaceutically acceptable salt thereof according to claim 6, wherein the halogen is fluorine or chlorine.

12. The compound, or a stereoisomer or tautomer thereof, or a pharmaceutically acceptable salt thereof according to claim 6, wherein the $C_1$-$C_3$ alkyl is methyl.

13. The method according to claim 10, wherein the disease is a cancer.

14. The method according to claim 13, wherein the cancer is lung cancer, thyroid cancer, colon cancer, breast cancer or pancreatic cancer.

* * * * *